US010751383B2

(12) United States Patent
Barriere et al.

(10) Patent No.: US 10,751,383 B2
(45) Date of Patent: Aug. 25, 2020

(54) DOSES AND METHODS FOR ADMINISTERING TELAVANCIN

(71) Applicant: Cumberland Pharmaceuticals Inc., Nashville, TN (US)

(72) Inventors: Steven L. Barriere, San Francisco, CA (US); Arthur Lo, San Francisco, CA (US); Mathai Mammen, Menlo Park, CA (US); Philip Worboys, San Mateo, CA (US)

(73) Assignee: CUMBERLAND PHARMACEUTICALS INC., Nashville, TN (US)

( * ) Notice: Subject to any disclaimer, the term of this patent is extended or adjusted under 35 U.S.C. 154(b) by 0 days.

(21) Appl. No.: 15/945,126

(22) Filed: Apr. 4, 2018

(65) Prior Publication Data

US 2018/0236027 A1   Aug. 23, 2018

Related U.S. Application Data

(62) Division of application No. 15/046,664, filed on Feb. 18, 2016, now abandoned.

(60) Provisional application No. 62/119,592, filed on Feb. 23, 2015.

(51) Int. Cl.
| | |
|---|---|
| *A61K 38/12* | (2006.01) |
| *A61K 38/14* | (2006.01) |
| *A61K 9/00* | (2006.01) |
| *A61K 47/40* | (2006.01) |

(52) U.S. Cl.
CPC ............ *A61K 38/14* (2013.01); *A61K 9/0019* (2013.01); *A61K 38/12* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 6,635,618 | B2 | 10/2003 | Leadbetter et al. |
| 6,872,701 | B2 | 3/2005 | Leadbetter et al. |
| 7,008,923 | B2 | 3/2006 | Leadbetter et al. |
| 7,208,471 | B2 | 4/2007 | Leadbetter |
| 7,351,691 | B2 | 4/2008 | Leadbetter et al. |
| 7,531,623 | B2 | 5/2009 | Liu et al. |
| 7,700,550 | B2 | 4/2010 | Leadbetter |
| 8,101,575 | B2 | 1/2012 | Leadbetter |
| 2016/0058750 | A1 | 3/2016 | Duffy |

FOREIGN PATENT DOCUMENTS

WO   2005042568 A2   5/2005

OTHER PUBLICATIONS

Lodise et al., "Telavancin Pharmacokinetics and Pharmacodynamics in Patients with Complicated Skin and Skin Structure Infections and Various Degrees of Renal Function", Antimicrobial Agents and Chemotherapy, 2011, 2062-2066 (Year: 2011).*
FDA, "Telavancin for the Treatment of Complicated Skin and Skin Structure Infections", FDA Briefing Document for Anti-Infective Drug Advisory Committee Meeting, 2008, 84 pages (Year: 2008).*
The European Medicines Agency,"VIBATIV-Assessment report", pp. 1-110, 2011 (Year: 2011).*
Attwood et al., "Telavancin: A novel lipoglycopeptide antimicrobial agent", Am. J. Health-Syst. Pharm., 64, 2335-2348 (Nov. 15, 2007).
Barriere et al., "Effects of a new antibacterial, Telavancein, on cardiac repolarization (QTc interval duration) in healthy subjects", J. Clin. Pharmacol., 2004, 44:689-695.
Cada et al., "Formulary Drug Reviews—Telavancin", Hosp. Pharm., 2010, 45(2):142-149.
Charneski et al., "Telavancin: A novel lipoglycopeptide antibiotic", Ann. Pharmacother., 2009, 43:928-938.
Corey et al., "Telavancin for hospital-acquired pneumonia: clinical response and 28-day survival", Antimicrob. Agents Chemother., 2014, 58(4):2030-2037.
"Telavancin—TD 6424, TD-6424", Drugs R D, 2006, 7(6):384-388.
Hegde et al., "Pharmacodynamics of Telavancin (TD-6424), a novel bactericidal agent, against gram-positive bacteria", Antimicrob. Agents Chemother., 2004, 48(8):3043-3050.
Kanafani, "Telavancin: a new lipoglycopeptide with multiple mechanisms of action", Expert Rev. Anti. Infect. Ther., 4(5), 743-749 (2006).
Laohavaleeson et al., "Telavancin: a novel lipoglycopeptide for serious gram-positive infections", Expert Opin. Investig. Drugs, (2007), 16(3):347-357.
Lodise et al., "Telavancin pharmacokinetics and pharmacodynamics in patients with complicated skin and skin structure infections and various degrees of renal function", Antimicrob. Agents Chemother., 2012, 56(4):2062-2066.
Nannini et al., "A new lipoglycopeptide: Telavancin", Expert Opin. Pharmacother., (2008) 9(12):2197-2207.
Nannini et al., "Telavancin for the treatment of hospital-acquired pneumonia: findings from the ATTAIN studies", Expert Rev. Anti. Infect. Ther., 10(8), 847-854 (2012).
Pace et al., "Telavancin Theravance", Curr. Opin. Investig. Drugs, 2005, 6(2), 216-225.
Plotkin et al., "Telavancin (Vibativ), a new option for the treatment of gram-positive infections", Drug Forecast, 36(3), 127-138 (2011).

(Continued)

*Primary Examiner* — Lianko G Garyu
(74) *Attorney, Agent, or Firm* — Vivicar Law, PLLC

(57) ABSTRACT

Doses and methods for administering telavancin or a pharmaceutically-acceptable salt thereof to a human patient having an infection caused by *Staphylococcus aureus*, such as bacteremia, pneumonia, endocarditis, osteomyelitis, a prosthetic joint infection or a complicated skin and skin structure infection, are disclosed. Also disclosed are methods for treating an infection caused by *Staphylococcus aureus* in a human patient using telavancin or a pharmaceutically-acceptable salt thereof. The dose of telavancin administered to the patient is determined, in part, by the weight and creatinine clearance of the patient.

5 Claims, 21 Drawing Sheets

(56) References Cited

OTHER PUBLICATIONS

Rubinstein et al., "Telavancin for the treatment of serious gram-positive infections, including hospital acquired pneumonia", Expert Opin. Pharmacother., (2011) 12(17):2737-2750.
Samara et al., "Population pharmacokinetics of Telavancin in healthy subjects and patients with infections", Antimicrob. Agents Chemother., 2012, 56(4):2067-2073.
Shaw et al., "Pharmacokinetics, serum inhibitory and bactericidal activity, and safety of telavancin in healthy subjects", Antimicrob. Agents Chemother., 2005, 49(1):195-201.
Stryjewski et al., "Telavancin versus standard therapy for treatment of complicated skin and skin structure infections caused by gram-positive bacteria: FAST 2 study", Antimicrob. Agents Chemother., 2006, 50(3):862-867.
Stryjewski et al., "Telavancin versus standard therapy for treatment of complicated skin and soft-tissue infections due to gram-positive bacteria", Clin. Infect. Dis., 2005, 40:1601-1607.
Stryjewski et al., "Telavancin versus vancomycin for the treatment of complicated skin and skin-structure infections caused by gram-positive organisms", Clin. Infect. Dis., 2008, 46:1683-1693.
VIBATIV (Telavancin), Prescribing Information (Revised Mar. 2014).
Wong et al., "Multiple-dose pharmacokinetics of intravenous telavancin in healthy male and female subjects", J. Antimicrob. Chemother., 2008, 62:780-783.
Marcos et al., "Acute renal insufficiency during Telavancin therapy in clinical practice", J. Antimicrob. Chemother., 67, 723-726 (2012).
Pai, "Comment on: Acute renal insufficiency during Telavancin therapy in clinical practice", J. Antimicrob. Chemother., 67, 1300 (2012).
Saraf et al., "Telavancin, a new lipoglycopeptide antimicrobial, in complicated skin and soft tissue infections", Infection and Drug Resistance, 4:87-95 (2011).
International Search Report for PCT/2016/018396.
Written Opinion for PCT/2016/018396.
FDA, "Telavancin for the treatment of complicated skin and skin structure infections", FDA Briefing Document for Anti-Infective Drugs Advisory Committee Meeting, Nov. 19, 2008, pp. 1-84 (2008).
Walpole et al., "The weight of nations: an estimation of adult human biomass", BMC Public Health, pp. 1-6 (2012).

\* cited by examiner

VERTICAL LINE INDICATES THE $AUC_{0-24h}$ CUTPOINT OF 767 μg·hr/mL

VERTICAL LINE INDICATES THE $AUC_{0-24h}$ BREAKPOINT OF 767 μg*hr/mL)

SOLID LINE INDICATES PREDICTED PROBABILITY OF EVENT; SHADED AREAS INDICATE 95% CONFIDENCE INTERVAL.

SOLID LINE INDICATES PREDICTED PROBABILITY OF EVENT; SHADED AREAS INDICATE 95% CONFIDENCE INTERVAL.

SOLID LINE INDICATES PREDICTED PROBABILITY OF MORTALITY;
SHADED AREAS INDICATE 95% CONFIDENCE INTERVAL.

SOLID LINE INDICATES PREDICTED PROBABILITY OF EVENT;
SHADED AREAS INDICATE 95% CONFIDENCE INTERVAL.

SOLID LINE INDICATES PREDICTED PROBABILITY OF EVENT; SHADED AREAS INDICATE 95% CONFIDENCE INTERVAL.

DOSES AND METHODS FOR ADMINISTERING TELAVANCIN

CROSS-REFERENCE TO RELATED APPLICATIONS

This application claims the benefit of U.S. Provisional Application No. 62/119,592, filed on Feb. 23, 2015; the entire disclosure of which is incorporated herein by reference in its entirety.

BACKGROUND OF THE INVENTION

Field of the Invention

The present invention relates to novel doses and methods for administering telavancin or a pharmaceutically-acceptable salt thereof to a human patient having an infection caused by *Staphylococcus aureus*, such as bacteremia, pneumonia, endocarditis, osteomyelitis, a prosthetic joint infection or a complicated skin and skin structure infection. The present invention also relates to methods for treating an infection caused by *Staphylococcus aureus* in a human patient using telavancin or a pharmaceutically-acceptable salt thereof. In the present invention, the dose of telavancin administered to the patient is determined, in part, by the weight and creatinine clearance of the patient.

State of the Art

Telavancin is a lipoglycopeptide antibacterial agent used to treat infections caused by susceptible Gram-positive bacteria in human patients, such as complicated skin and skin structure infections (cSSSI) and hospital-acquired and ventilator-associated bacterial pneumonia (HABP/VABP). See, for example, Pace et al., *Curr. Opin. Investig. Drugs* (2005) 6(2):216-25; *Drugs R D.* (2006) 7(6):384-8; Kanafani, *Expert Rev. Anti. Infect. Ther.* (2006) 4(5):743-9; Attwood et al., *Am. J. Health Syst. Pharm.* (2007) 64(22): 2335-48; Laohavaleeson et al., *Expert Opin. Investig. Drugs* (2007) 16(3):347-57; Nannini et al., *Expert Opin. Pharmacother.* (2008) 9(12):2197-207; Charneski et al., *Ann. Pharmacother.* (2009) 43(5):928-38; Rubinstein et al., *Expert Opin. Pharmacother.* (2011) 12(17):2737-50; Nannini et al., *Expert Review of Antiinfective Therapy* (2012) 10(8):847-54. Telavancin is also being evaluated for use in treating complicated bacteremia caused by *Staphylococcus aureus*.

For most cSSSI and HABP/VABP patients with normal renal function, the currently-recommended dose of telavancin is 10 mg/kg (free base equivalents) every 24 hours. See, for example, VIBATIV® (telavancin) Prescribing Information; Revised March 2014. However, because telavancin is eliminated primarily by the kidney, a dose adjustment is recommended for patients whose creatinine clearance is less than or equal to 50 mL/min. For adult patients having a creatinine clearance between 30 mL/min and 50 mL/min, the currently-recommended dose of telavancin is 7.5 mg/kg every 24 hours; and for adult patients with a creatinine clearance between 10 mL/min and less than 30 mL/min, the dose is further adjusted to 10 mg/kg every 48 hours.

Even with the prior dose adjustments for adult patients with renal impairment, increased rates of acute kidney injury and mortality (in HABP/VABP patients with moderate or severe renal impairment) were observed in clinical trials for telavancin compared to vancomycin. See, for example, Rubinstein et al., *Expert Opin. Pharmacother.* (2011) 12(17):2737-50.

Accordingly, a need exists for new doses and methods for administering telavancin to human patients that are predicted to reduce the overall incidence of acute kidney injury and mortality in such patients while maintaining the antibacterial efficacy of telavancin.

SUMMARY OF THE INVENTION

The present invention provides new doses and methods for administering telavancin or a pharmaceutically-acceptable salt thereof to a human patient having an infection caused by *Staphylococcus aureus*, such as bacteremia, pneumonia, endocarditis, osteomyelitis, a prosthetic joint infection or a complicated skin and skin structure infection.

In one embodiment, the present invention is based, in part, on the discovery that acute kidney injury and mortality are predicted to be reduced and antibacterial efficacy is predicted to be maintained if (i) the dose of telavancin administered to the patient is about 25 percent lower than the prior dose based on the patient's creatinine clearance and (ii) the total amount of telavancin administered to the patient per day does not exceed a specified amount based on the patient's weight and creatinine clearance. Additionally, for those patients having a creatinine clearance less than about 30 mL/minute, acute kidney injury and mortality are also predicted to be reduced if the present dose of telavancin is administered every 24 hours instead of every 48 hours as is recommended for the prior dose. Surprisingly, by using the dosing regimens of the present invention, retrospective analyses predict that the efficacy of telavancin will be maintained and the overall incidence of acute kidney injury and mortality will be reduced.

Accordingly, in one aspect, the present invention provides a once-daily dose of telavancin for administration to a human patient having bacteremia, pneumonia, endocarditis, osteomyelitis, or a prosthetic joint infection caused by *Staphylococcus aureus*, the dose comprising telavancin or a pharmaceutically-acceptable salt thereof in an amount selected from:

(a) about 7.5 mg/kg of telavancin (free base equivalents) if the patient has a creatinine clearance greater than about 50 mL/minute, provided that the total dose does not exceed about 750 mg/day;

(b) about 5.6 mg/kg of telavancin (free base equivalents) if the patient has a creatinine clearance between about 30 mL/minute and about 50 mL/minute, provided that the total dose does not exceed about 560 mg/day; and (c) about 3.8 mg/kg of telavancin (free base equivalents) if the patient has a creatinine clearance less than about 30 mL/minute, provided that the total dose does not exceed about 380 mg/day.

In another aspect, the present invention provides a method for administering telavancin to a human patient having bacteremia, pneumonia, endocarditis, osteomyelitis, or a prosthetic joint infection caused by *Staphylococcus aureus*, the method comprising administering a dose of telavancin or a pharmaceutically-acceptable salt thereof to the patient about once every 24 hours; wherein the dose of telavancin administered to the patient is selected from:

(a) about 7.5 mg/kg of telavancin (free base equivalents) if the patient has a creatinine clearance greater than about 50 mL/minute, provided that the total dose does not exceed about 750 mg/day;

(b) about 5.6 mg/kg of telavancin (free base equivalents) if the patient has a creatinine clearance between about 30 mL/minute and about 50 mL/minute, provided that the total dose does not exceed about 560 mg/day; and (c) about 3.8 mg/kg of telavancin (free base equivalents) if the patient has a creatinine clearance less than about 30 mL/minute, provided that the total dose does not exceed about 380 mg/day.

In yet another aspect, the present invention provides a method for treating bacteremia, pneumonia, endocarditis, osteomyelitis, or a prosthetic joint infection caused by *Staphylococcus aureus* in a human patient, the method comprising administering a dose of telavancin or a pharmaceutically-acceptable salt thereof to the patient about once every 24 hours; wherein the dose of telavancin administered to the patient is selected from:

(a) about 7.5 mg/kg of telavancin (free base equivalents) if the patient has a creatinine clearance greater than about 50 mL/minute, provided that the total dose does not exceed about 750 mg/day;

(b) about 5.6 mg/kg of telavancin (free base equivalents) if the patient has a creatinine clearance between about 30 mL/minute and about 50 mL/minute, provided that the total dose does not exceed about 560 mg/day; and (c) about 3.8 mg/kg of telavancin (free base equivalents) if the patient has a creatinine clearance less than about 30 mL/minute, provided that the total dose does not exceed about 380 mg/day.

In separate and distinct embodiments for each of these doses and methods, in one embodiment, the patient has a creatinine clearance greater than about 50 mL/minute. In one embodiment, the patient has a creatinine clearance between about 30 mL/minute and about 50 mL/minute. In one embodiment, the patient has a creatinine clearance less than about 30 mL/minute. And in one embodiment, the patient has a creatinine clearance between about 10 mL/minute and less than about 30 mL/minute.

In one embodiment, the patient has bacteremia. In one embodiment, the dose is administered for about 4 to about 6 weeks.

In one embodiment, the patient has pneumonia. In one embodiment, the dose is administered for about 7 to about 14 days.

In one embodiment, the patient has endocarditis. In one embodiment, the dose is administered for about 4 to about 6 weeks.

In one embodiment, the patient has osteomyelitis. In one embodiment, the dose is administered for about 4 to about 8 weeks.

In one embodiment, the patient has a prosthetic joint infection. In one embodiment, the dose is administered for about 2 to about 8 weeks.

In one embodiment, the dose is administered intravenously.

In one embodiment, the *Staphylococcus aureus* is methicillin-resistant *Staphylococcus aureus*.

In one embodiment, the telavancin is administered as a hydrochloride salt.

In one embodiment, the telavancin or a pharmaceutically-acceptable salt thereof is administered in combination with 2-hydroxypropyl-β-cyclodextrin.

In another aspect, the present invention provides a once-daily dose of telavancin for administration to a patient having a creatinine clearance less than about 50 mL/minute and having a complicated skin and skin structure infection caused by *Staphylococcus aureus*, the dose comprising telavancin or a pharmaceutically-acceptable salt thereof in an amount selected from:

(a) about 5.6 mg/kg of telavancin (free base equivalents) if the patient has a creatinine clearance between about 30 mL/minute and about 50 mL/minute, provided that the total dose does not exceed about 560 mg/day; and (b) about 3.8 mg/kg of telavancin (free base equivalents) if the patient has a creatinine clearance less than about 30 mL/minute, provided that the total dose does not exceed about 380 mg/day.

In yet another aspect, the present invention provides a method for administering telavancin to a human patient having a creatinine clearance less than about 50 mL/minute and having a complicated skin and skin structure infection caused by *Staphylococcus aureus*, the method comprising administering a dose of telavancin or a pharmaceutically-acceptable salt thereof to the patient about once every 24 hours; wherein the dose of telavancin administered to the patient is selected from:

(a) about 5.6 mg/kg of telavancin (free base equivalents) if the patient has a creatinine clearance between about 30 mL/minute and about 50 mL/minute, provided that the total dose does not exceed about 560 mg/day; and (b) about 3.8 mg/kg of telavancin (free base equivalents) if the patient has a creatinine clearance less than about 30 mL/minute, provided that the total dose does not exceed about 380 mg/day.

In still another aspect, the present invention provides a method for treating a complicated skin and skin structure infection caused by *Staphylococcus aureus* in a human patient having a creatinine clearance less than about 50 mL/minute, the method comprising administering a dose of telavancin or a pharmaceutically-acceptable salt thereof to the patient about once every 24 hours; wherein the dose of telavancin administered to the patient is selected from:

(a) about 5.6 mg/kg of telavancin (free base equivalents) if the patient has a creatinine clearance between about 30 mL/minute and about 50 mL/minute, provided that the total dose does not exceed about 560 mg/day; and (b) about 3.8 mg/kg of telavancin (free base equivalents) if the patient has a creatinine clearance less than about 30 mL/minute, provided that the total dose does not exceed about 380 mg/day.

In separate and distinct embodiments for each of these doses and methods, in one embodiment, the patient has a creatinine clearance between about 30 mL/minute and about 50 mL/minute. In one embodiment, the patient has a creatinine clearance less than about 30 mL/minute. In one embodiment, the patient has a creatinine clearance between about 10 mL/minute and less than about 30 mL/minute.

In one embodiment, the dose is administered for about 7 to about 14 days.

In one embodiment, the dose is administered intravenously.

In one embodiment, the *Staphylococcus aureus* is methicillin-resistant *Staphylococcus aureus*.

In one embodiment, the telavancin is administered as a hydrochloride salt.

In one embodiment, telavancin or a pharmaceutically-acceptable salt thereof is administered in combination with 2-hydroxypropyl-β-cyclodextrin.

In another aspect, the present invention provides a once-daily dose of telavancin for administration to a human patient having an infection caused by *Staphylococcus aureus*, the dose comprising an amount of telavancin (free base equivalents) in the range defined by formula (I):

$$\text{Dose (mg)} = AUC_{target} * 1.15 * (WT/77)^{0.352} * (CrCl/99)^{0.454} \pm 5.0 \quad \text{(I)}$$

wherein:

$AUC_{target}$ is a target area under the concentration curve selected from the range of about 220 to about 730 μg*hr/mL;

WT is the weight of the patient in kilograms; and

CrCl is the creatinine clearance of the patient in mL/minute.

In yet another aspect, the present invention provides a method for administering telavancin to a human patient having an infection caused by *Staphylococcus aureus*, the method comprising administering a dose of telavancin or a pharmaceutically-acceptable salt thereof to the patient about once every 24 hours; wherein the dose comprises an amount of telavancin (free base equivalents) in the range defined by formula (I).

In still another aspect, the present invention provides a method for treating an infection caused by *Staphylococcus aureus* in a human patient, the method comprising administering a dose of telavancin or a pharmaceutically-acceptable salt thereof to the patient about once every 24 hours; wherein the dose comprises an amount of telavancin (free base equivalents) in the range defined by formula (I).

In another aspect, the present invention provides a once-daily dose of telavancin for administration to a human patient having an infection caused by *Staphylococcus aureus*, the dose comprising an amount of telavancin (free base equivalents) selected from a nomogram wherein each value in the nomogram is in the range defined by formula (I).

In yet another aspect, the present invention provides a method for administering telavancin to a human patient having an infection caused by *Staphylococcus aureus*, the method comprising administering a dose of telavancin or a pharmaceutically-acceptable salt thereof to the patient about once every 24 hours; wherein the dose comprises an amount of telavancin (free base equivalents) selected from a nomogram wherein each value in the nomogram is in the range defined by formula (I).

In still another aspect, the present invention provides a method for treating an infection caused by *Staphylococcus aureus* in a human patient, the method comprising administering a dose of telavancin or a pharmaceutically-acceptable salt thereof to the patient about once every 24 hours; wherein the dose comprises an amount of telavancin (free base equivalents) selected from a nomogram wherein each value in the nomogram is in the range defined by formula (I).

In separate and distinct embodiments for each of these doses and methods, in one embodiment, the once-daily dose defined by formula (I) is rounded to the nearest 10 mg.

In one embodiment, the $AUC_{target}$ is 600 μg*hr/mL.

In one embodiment, the patient has bacteremia. In one embodiment, the dose is administered for about 4 to about 6 weeks.

In one embodiment, the patient has pneumonia. In one embodiment, the dose is administered for about 7 to about 14 days.

In one embodiment, the patient has endocarditis. In one embodiment, the dose is administered for about 4 to about 6 weeks.

In one embodiment, the patient has osteomyelitis. In one embodiment, the dose is administered for about 4 to about 8 weeks.

In one embodiment, the patient has a prosthetic joint infection. In one embodiment, the dose is administered for about 2 to about 8 weeks.

In one embodiment, the patient has a complicated skin and skin structure infection. In one embodiment, the dose is administered for about 7 to about 14 days.

In one embodiment, the dose is administered intravenously.

In one embodiment, the *Staphylococcus aureus* is methicillin-resistant *Staphylococcus aureus*.

In one embodiment, the telavancin is administered as a hydrochloride salt.

In one embodiment, the telavancin or a pharmaceutically-acceptable salt thereof is administered in combination with 2-hydroxypropyl-β-cyclodextrin.

In another aspect, the present invention provides a once-daily dose of telavancin for administration to a human patient having an infection caused by *Staphylococcus aureus*, the dose comprising an amount of telavancin (free base equivalents) selected from a nomogram comprising the values:

|    |     | CrCl |     |     |     |     |     |     |     |     |
|----|-----|------|-----|-----|-----|-----|-----|-----|-----|-----|
|    | mg  | 10   | 20  | 30  | 40  | 50  | 70  | 90  | 120 | 150 |
| WT | 50  | 210  | 290 | 340 | 390 | 430 | 510 | 570 | 650 | 720 |
|    | 60  | 220  | 310 | 370 | 420 | 460 | 540 | 610 | 690 | 760 |
|    | 70  | 240  | 320 | 390 | 440 | 490 | 570 | 640 | 730 | 810 |
|    | 90  | 260  | 350 | 420 | 480 | 530 | 620 | 700 | 800 | 880 |
|    | 110 | 280  | 380 | 450 | 520 | 570 | 670 | 750 | 850 | 940 |
|    | 130 | 290  | 400 | 480 | 550 | 610 | 710 | 790 | 910 | 1000 |
|    | 150 | 310  | 420 | 510 | 580 | 640 | 750 | 840 | 950 | 1050 | wherein:

WT is the weight of the patient in kilograms (rounded to the nearest value in the nomogram); and CrCl is the creatinine clearance of the patient in mL/minute (rounded to the nearest value in the nomogram).

In yet another aspect, the present invention provides a method for administering telavancin to a human patient having an infection caused by *Staphylococcus aureus*, the method comprising administering a dose of telavancin or a pharmaceutically-acceptable salt thereof to the patient about once every 24 hours; wherein the dose comprises an amount of telavancin (free base equivalents) selected from the nomogram above.

In still another aspect, the present invention provides a method for treating an infection caused by *Staphylococcus aureus* in a human patient, the method comprising administering a dose of telavancin or a pharmaceutically-acceptable salt thereof to the patient about once every 24 hours; wherein the dose comprises an amount of telavancin (free base equivalents) selected from the nomogram above.

In separate and distinct embodiments for each of these doses and methods, in one embodiment, the patient has bacteremia. In one embodiment, the dose is administered for about 4 to about 6 weeks.

In one embodiment, the patient has pneumonia. In one embodiment, the dose is administered for about 7 to about 14 days.

In one embodiment, the patient has endocarditis. In one embodiment, the dose is administered for about 4 to about 6 weeks.

In one embodiment, the patient has osteomyelitis. In one embodiment, the dose is administered for about 4 to about 8 weeks.

In one embodiment, the patient has a prosthetic joint infection. In one embodiment, the dose is administered for about 2 to about 8 weeks.

In one embodiment, the patient has a complicated skin and skin structure infection. In one embodiment, the dose is administered for about 7 to about 14 days.

In one embodiment, the dose is administered intravenously.

In one embodiment, the *Staphylococcus aureus* is methicillin-resistant *Staphylococcus aureus*.

In one embodiment, the telavancin is administered as a hydrochloride salt.

In one embodiment, the telavancin or a pharmaceutically-acceptable salt thereof is administered in combination with 2-hydroxypropyl-β-cyclodextrin.

Other aspects and embodiments of this invention are disclosed herein.

BRIEF DESCRIPTION OF THE DRAWINGS

Various aspects of the present invention are illustrated by reference to the accompanying drawings.

In FIG. 1 and FIG. 2, the black point indicates the median, the top and bottom of the box indicate the lower and upper quartiles (25% and 75%), the whiskers indicate the upper and lower data within 1.5 times the interquartile range, and the box width indicates the number of subjects in each category (there were no outliers).

DETAILED DESCRIPTION OF THE INVENTION

Figure 1:
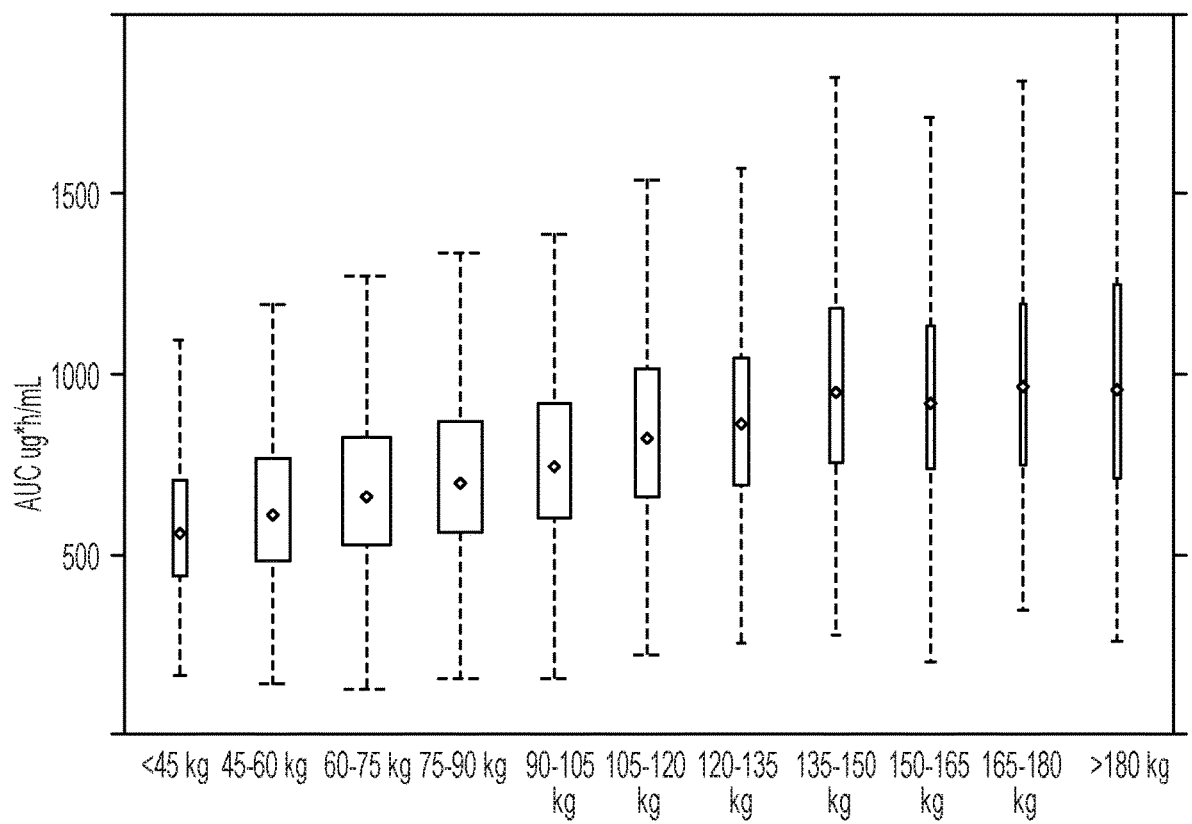
FIG. 1 shows the predicted $AUC_{0-24h}$ of the prior dosing regimen as a function of weight.

Amongst various aspects and embodiments, the present invention provides doses and methods for administering telavancin or a pharmaceutically-acceptable salt thereof; and methods for treating an infection caused by *Staphylococcus aureus,* such as bacteremia, pneumonia, endocarditis, osteomyelitis, a prosthetic joint infection or a complicated skin and skin structure infection, in a human patient using telavancin or a pharmaceutically-acceptable salt thereof.

Definitions

When describing this invention, the following terms have the following meanings unless otherwise indicated.

The term "free base equivalent(s)" means the amount of free base in an acid addition salt of the free base and an acid (i.e., the amount of free base if the acid addition salt form was converted to the free base form). For example, one gram of telavancin dihydrochloride salt (MW=1828.5) contains 0.96 grams of telavancin (MW=1755.63) and 0.04 grams of hydrogen chloride (MW=36.46); or 0.96 grams of telavancin free base equivalents.

The term "pharmaceutically-acceptable salt" means a salt that is acceptable for administration to a human patient (e.g., salts having acceptable mammalian safety for a given dosage regime). Representative pharmaceutically-acceptable salts of telavancin include acid addition salts of telavancin with acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "present dose" or "present dosing regimen" or "new dose" or "new dosing regimen" refers to a dose or dosing regimen of the present invention.

The term "prior dose" or "prior dosing regimen" refers to an existing or prior art dose or dosing regimen, such as the dosing regimen set forth in the VIBATIV® (telavancin) Prescribing Information; Revised March 2014.

The term "telavancin" means the compound $N^{3''}$-[2-(decylamino)ethyl]-29-[[(phosphonomethyl)amino]methyl] vancomycin having the formula:

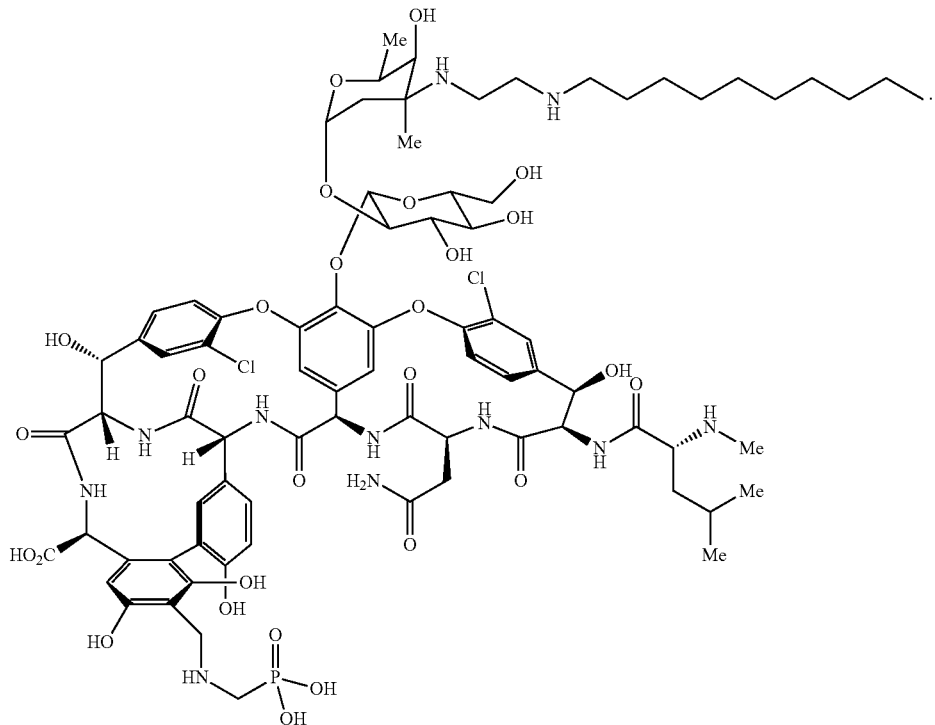

The term "telavancin hydrochloride" means any hydrochloride salt of telavancin, including, for example, the mono-, di- and trihydrochloride salts of telavancin and mixtures thereof (e.g., x·HCl, where x is 1 to 3).

In one embodiment, the present invention is based, in part, on the discovery that rates of acute kidney injury and mortality are predicted to be reduced and antibacterial efficacy is predicted to be maintained if:

(i) the dose of telavancin administered to a patient is about 25 percent lower than the currently recommended dose based on the patient's creatinine clearance;

(ii) the total amount of telavancin administered to a patient per day does not exceed a specified amount based on the patient's creatinine clearance; and (iii) for those patients having a creatinine clearance less than about 30 mL/minute, rates of acute kidney injury and mortality are predicted to be reduced if the dose of telavancin is administered every 24 hours instead of every 48 hours as is currently recommended.

This discovery is based, in part, on retrospective analyses of the Phase 3 clinical studies for telavancin for cSSSI and HABP/VABP. Based on these analyses, higher exposures to telavancin were found to be associated with a higher probability of mortality in HABP/VABP subjects with moderate or severe impairment in renal function and a higher likelihood of AKI in cSSSI subjects. However, for all HABP/VABP and cSSSI subjects, no relationship between exposure and clinical response at test of cure was identified. This is likely due to the range of exposures being sufficiently high so as not to compromise clinical efficacy. Based on these exposure-response analyses, the doses of the present invention are expected to reduce the risk of acute kidney injury in all patients and mortality in patients with moderate to severe renal impairment while not affecting efficacy.

Additionally, analyses of the clinical data have shown a good correlation between the pharmacokinetics of telavancin with the weight and creatinine clearance of the patients. This correlation provides a formula for determining a once-daily dose of telavancin based on a target AUC and the patient's weight and creatinine clearance. Accordingly, in another embodiment, the present invention is based, in part, on the discovery that rates of acute kidney injury and mortality are predicted to be reduced and antibacterial efficacy is predicted to be maintained if the dose of telavancin (free base equivalents) is based on formula (i):

$$\text{Does (mg)} = AUC_{target} * 1.15 * (WT/77)^{0.352} * (CrCl/99)^{0.454} \quad (i)$$

where:

$AUC_{target}$ is the target area under the concentration curve in µg·hr/mL;

WT is the weight of the patient in kilograms; and

CrCl is the creatinine clearance of the patient in mL/minute.

In one embodiment, the dose determined by formula (i) is a range of ±5 mg of the dose amount calculated by formula (i). In another embodiment, the dose determined by formula (i) is rounded to the nearest 10 mg.

In another embodiment, formula (i) is used to create a nomogram or look-up-table to quickly determine the appropriate dose for a targeted AUC based on the patient's weight and creatinine clearance. In one embodiment, the dose determined by the formula is rounded to the nearest 10 mg when used in the nomogram.

Telavancin Drug Substance

Telavancin or any pharmaceutically-acceptable salt of telavancin can be employed in this invention. In one embodiment, telavancin hydrochloride is used. Telavancin hydrochloride is an off-white to slightly colored amorphous powder with the empirical formula $C_{80}H_{106}C_{12}N_{11}O_{27}P\cdot xHCl$ (where x=1 to 3). In a particular embodiment, telavancin dihydrochloride is used.

Telavancin and telavancin hydrochloride salts can be prepared by methods and processes known in the art. See, for example, U.S. Pat. Nos. 6,635,618 B2; 6,872,701 B2; 6,887,976 B2; 6,979,723 B2; 7,015,305 B2; 7,015,307 B2; 7,074,890 B2; 7,160,984 B2; 7,208,471 B2; 7,301,004 B2; 7,375,181 B2; 7,468,420 B2; 7,531,623 B2; 7,858,583 B2; 8,003,755 B2; and 8,093,354 B2.

Telavancin Drug Product

Telavancin is typically employed in this invention as a pharmaceutical composition comprising telavancin or a pharmaceutically-acceptable salt thereof and one or more excipients or carriers. Any suitable excipients or carriers may be used. In one embodiment, the pharmaceutical composition is a storage-stable formulation suitable for reconstitution prior to administration to the patient.

For example, telavancin hydrochloride is commercially-available under the trademark VIBATIV® (telavancin) as a sterile, preservative-free, white to slightly colored lyophilized powder containing telavancin hydrochloride, 2-hydroxypropyl-β-cyclodextrin and mannitol. The product is available in single-use 250 mg and 750 mg strength vials. The 250 mg strength vial contains telavancin hydrochloride (equivalent to 250 mg of telavancin as the free base); 2500 mg of 2-hydroxypropyl-β-cyclodextrin (Hydroxypropyl-betadex, Ph. Eur.); and 312.5 mg of mannitol. The 750 mg strength vial contains telavancin hydrochloride (equivalent to 750 mg of telavancin as the free base); 7500 mg of 2-hydroxypropyl-β-cyclodextrin (Hydroxypropylbetadex, Ph. Eur.); and 937.5 mg of mannitol. When reconstituted, these pharmaceutical compositions form a clear to slightly colored solution with a pH of about 4.5±0.5.

Determination of the Dose

The dose of telavancin to be administered to a patient is determined based on the body weight and creatinine clearance of the patient; and in some embodiments, by the target AUC.

The patient's body weight is determined using any conventional means for measuring weight such as a scale. For example, a patient's body weight can be determined using a built-in bed scale, a wheel-chair scale, a digital standing scale, a mechanical standing scale and the like. Representative patient body weights are typically in the range of from about 30 to about 320 kg.

The patient's creatinine clearance (CrCl) is typically estimated using the Cockcroft-Gault formula:

$$CrCl = \frac{[140 - \text{age (years)}] \times \text{ideal body weight (kg)}^*}{[72 \times \text{serum creatinine (mg/dL)}]}$$

{×0.85 for female patients}

*Use actual body weight if < ideal body weight

See, e.g., Cockcroft et al., *Nephron*. 1976, 16(1), 31-41.

The patient's ideal body weight is typically determined using the Devine formula:

$$IBW \text{ (male)} = 50 \text{ kg} + 0.9 \text{ kg/cm over 152 cm in height}$$

$$IBW \text{ (female)} = 45.5 \text{ kg} + 0.9 \text{ kg/cm over 152 cm in height}$$

As noted in the Cockcroft-Gault formula, if the patient's actual body weight is less than the ideal body weight, then the actual body weight is used in the formula.

A patient's serum creatinine is determined using any conventional blood test for measuring serum creatinine, such as those described in Israni A K, Kasiske B L. Laboratory assessment of kidney disease: filtration rate, urinalysis, and proteinuria. In: Taal M W, Chertow G M, Marsden P A, et al., eds. *Brenner and Rector's The Kidney*. 9th ed. Philadelphia, Pa: Elsevier Saunders; 2011:chap 25.

Representative patient creatinine clearance values are typically in the range of from about 3 to about 200 mL/minute; including about 3 to about 150 mL/minute.

In one embodiment, once the patient's body weight and creatinine clearance are determined, the daily dose of telavancin for the patient is determined as shown in Table I:

TABLE I

Dose of Telavancin Based on Creatinine Clearance and Body Weight

| Creatinine Clearance mL/min | Dose of Telavancin mg/kg | Not to Exceed mg/day |
|---|---|---|
| >50 | 7.5 | 750 |
| 30-50 | 5.6 | 560 |
| <30 | 3.8 | 380 |

In one embodiment, >50 mL/minute includes the range about 50 mL/minute to about 200 mL/minute. In one embodiment, <30 mL/minute includes the range about 10 mL/minute to less than about 30 mL/minute.

For example, a patient having a creatinine clearance of about 100 mL/min and a body weight of about 70 kg would be given a daily dose of telavancin (free base equivalents) of about 525 mg (i.e., 70 kg×7.5 mg/kg=525 mg). Another patient having a creatinine clearance of about 40 mL/min and a body weight of about 70 kg would be given a daily dose of telavancin (free base equivalents) of about 392 mg (i.e., 70 kg×5.6 mg/kg=392 mg). And yet another patient having a creatinine clearance of about 20 mL/min and a body weight of about 70 kg would be given a daily dose of telavancin (free base equivalents) of about 266 mg (i.e., 70 kg×3.8 mg/kg=266 mg). In this embodiment, for patients having a body weight greater than 100 kg, the daily dose of telavancin (free base equivalents) is capped at a specified amount based on the patient's creatinine clearance. For patients having a creatinine clearance greater than 50 mL/min, the maximum daily dose of telavancin is 750 mg. For patients having a creatinine clearance of 30 to 50 mL/min, the maximum daily dose of telavancin is 560 mg; and for patients having a creatinine clearance less than 30 mL/min, the maximum daily dose of telavancin is 380 mg.

For example, a patient having a creatinine clearance of about 100 mL/min and a body weight of about 120 kg would be given a daily dose of telavancin (free base equivalents) of about 750 mg, since the dose calculated based on the patient's body weight exceeds 750 mg (i.e., 120 kg×7.5 mg/kg=900 mg). Another patient having a creatinine clearance of about 40 mL/min and a body weight of about 120 kg would be given a daily dose of telavancin (free base equivalents) of about 560 mg, since the dose calculated based on the patient's body weight exceeds 560 mg (i.e., 120 kg×5.60 mg/kg=672 mg). And yet another patient having a creatinine clearance of about 20 mL/min and a body weight of about 120 kg would be given a daily dose of telavancin (free base equivalents) of about 380 mg, since the dose calculated based on the patient's body weight exceeds 380 mg (i.e., 120 kg×3.80 mg/kg=456 mg).

In another embodiment, the daily dose of telavancin for the patient is determined using formula (I):

$$\text{Dose (mg)} = AUC_{target} * 1.15 * (WT/77)^{0.352} * (CrCl/99)^{0.454} \pm 5.0 \quad (I)$$

wherein:

$AUC_{target}$ is a target area under the concentration curve selected from the range of about 220 to about 730 µg*hr/mL;

WT is the weight of the patient in kilograms; and

CrCl is the creatinine clearance of the patient in mL/minute.

The $AUC_{target}$ is typically determined by the physician treating the patient. In one embodiment, the $AUC_{target}$ is selected from the range of about 220 to about 730 µg*hr/mL. In another embodiment, the $AUC_{target}$ is selected from the range of about 450 to about 730 µg*hr/mL; including about 550 to about 700 µg*hr/mL. In another embodiment, the $AUC_{target}$ is selected from 450, 460, 470, 480, 490, 500, 510, 520, 530, 540, 550, 560, 570, 580, 590, 600, 610, 620, 630, 640, 650, 660, 670, 680, 690, 700, 710, 720 and 730; including 550, 600, 650 and 700 µg*hr/mL. In a particular embodiment, the $AUC_{target}$ is 600 µg*hr/mL.

Formula (I) provides a simple and accurate way for a physician to determine a personalized dose of telavanin (free base equivalents) based on the patient's weight and creatinine clearance. For example, using formula (I) and an $AUC_{target}$ of 600 µg*hr/mL, a patient having a creatinine clearance of about 100 mL/min and a body weight of about 70 kg would be given a daily dose of telavancin (free base equivalents) of about 667.2±5 mg; or rounded to the nearest 10 mg, about 670 mg. Another patient having a creatinine clearance of about 40 mL/min and a body weight of about 70 kg would be given a daily dose of telavancin (free base equivalents) of about 442.4±5 mg; or rounded to the nearest 10 mg, about 440 mg. And yet another patient having a creatinine clearance of about 20 mL/min and a body weight of about 70 kg would be given a daily dose of telavancin (free base equivalents) of about 322.9±5 mg; or rounded to the nearest 10 mg, about 320 mg.

In another embodiment, the daily dose of telavancin for the patient is determined by selecting the dose from a nomogram or look-up-table wherein each value in the nomogram is in the range defined by formula (I). For example, to prepare a nomogram using formula (I), an $AUC_{target}$ is selected, such as 600 µg*hr/mL. A table is then prepared using formula (I) and a series of patient weights and creatinine clearance values. For example, the following patient weights can be used: 40, 45, 50, 55, 60, 65, 70, 75, 80, 85, 90, 95, 100, 105, 110, 115, 120, 125, 130, 135, 140, 145, 150, 155, 160, 165 and 170 kilogram; or selections thereof. Similarly, the following creatinine clearance values can be used: 10, 15, 20, 25, 30, 35, 40, 45, 50, 55, 60, 65, 70, 75, 80, 85, 90, 95, 100, 105, 110, 115, 120, 125, 130, 135, 140, 145, and 150 mL/minute; or selections thereof. In one embodiment, the dose values listed in the nomogram are rounded to the nearest 10 mg.

For example, using an $AUC_{target}$ of 600 µg*hr/mL, the following representative nomogram was prepared using formula (I):

| WT mg | \multicolumn{9}{c}{CrCl} |
|---|---|---|---|---|---|---|---|---|---|

| mg | 10 | 20 | 30 | 40 | 50 | 70 | 90 | 120 | 150 |
|---|---|---|---|---|---|---|---|---|---|
| 50 | 210 | 290 | 340 | 390 | 430 | 510 | 570 | 650 | 720 |
| 60 | 220 | 310 | 370 | 420 | 460 | 540 | 610 | 690 | 760 |
| 70 | 240 | 320 | 390 | 440 | 490 | 570 | 640 | 730 | 810 |
| 90 | 260 | 350 | 420 | 480 | 530 | 620 | 700 | 800 | 880 |
| 110 | 280 | 380 | 450 | 520 | 570 | 670 | 750 | 850 | 940 |
| 130 | 290 | 400 | 480 | 550 | 610 | 710 | 790 | 910 | 1000 |
| 150 | 310 | 420 | 510 | 580 | 640 | 750 | 840 | 950 | 1050 | wherein:

WT is the weight of the patient in kilograms (rounded to the nearest value in the nomogram); and CrCl is the creatinine clearance of the patient in mL/minute (rounded to the nearest value in the nomogram).

A nomogram provides a simple and accurate way for a physician to determine a personalized dose of telavanin (free base equivalents) based on the patient's weight and creatinine clearance. For example, using this nomogram, a patient having a creatinine clearance of about 100 mL/min and a body weight of about 70 kg would be given a daily dose of telavancin (free base equivalents) of about 640 mg. Another patient having a creatinine clearance of about 40 mL/min and a body weight of about 70 kg would be given a daily dose of telavancin (free base equivalents) of about 440 mg. And yet another patient having a creatinine clearance of about 20 mL/min and a body weight of about 70 kg, would be given a daily dose of telavancin (free base equivalents) of about 320 mg.

Various nomograms can be prepared using formula (i) or formula (I) and all such nomograms are included within the scope of the present invention.

Once a patient begins treatment with telavancin, the patient's body weight and creatinine clearance are typically measured periodically, such as daily or weekly, and the dose of telavancin administered to the patient is adjusted, if necessary, using the new values to determine the proper dose of telavancin, e.g., using Table I, formula (I) or a nomogram.

Preparation and Administration of the Dose

Telavancin is typically administered to the patient by reconstituting the telavancin drug product and then further diluting the reconstituted mixture to form a dilute solution suitable for intravenous administration.

For example, a 250 mg vial of telavancin drug product can be reconstituted with 15 mL of 5% Dextrose Injection; Sterile Water for Injection; or 0.9% Sodium Chloride Injection. The resultant solution has a concentration of 15 mg/mL and total volume of about 17.0 mL.

Similarly, a 750 mg vial of telavancin drug product can be reconstituted with 45 mL of 5% Dextrose Injection; Sterile Water for Injection; or 0.9% Sodium Chloride Injection. The resultant solution has a concentration of 15 mg/mL and total volume of about 50.0 mL.

Once the telavancin drug product has been reconstituted (e.g., to 15 mg of telavancin (free base equivalents) per mL), the following formula can be used to calculate the volume of reconstituted VIBATIV solution required to prepare a dose:

$$\text{Volume of reconstituted solution (mL)} = \frac{\text{Telavancin dose (mg)}}{\text{Telavancin concentration (mg/mL)}}$$

For example, a 750 mg dose of telavancin would require 50 mL of reconstituted solution having a telavancin concentration of 15 mg/mL.

For doses of 150 to 750 mg, the appropriate volume of reconstituted solution is typically further diluted with 100 to 250 mL of an infusion solution prior to infusion. Alternatively, doses can be further diluted using a volume that results in a final concentration of 0.6 to 8 mg/mL. Representative infusion solutions include, for example, 5% Dextrose Injection; 0.9% Sodium Chloride Injection; Lactated Ringer's Injection; and the like.

The dosing solution is then typically administered to the patient by intravenous infusion over a period of about 60 minutes, including about 45 to about 75 minutes.

Treatment of Infections Caused by *Staphylococcus Aureus*

In one embodiment, the methods of this invention are used to treat bacteremia caused by *Staphylococcus aureus*, including uncomplicated bacteremia (UCB) and complicated bacteremia (CB). In this embodiment, telavancin will typically be dosed daily for about 2 to about 6 weeks, or until the bacteremia has been treated. In a particular embodiment, telavancin is dosed daily for about 4 to about 6 weeks.

In another embodiment, the methods of this invention are used to treat pneumonia caused by *Staphylococcus aureus*, including hospital-acquired bacterial pneumonia (HABP) and ventilator-associated bacterial pneumonia (VABP). In this embodiment, telavancin will typically be dosed daily for about 7 to about 14 days, or until the pneumonia has been treated.

In another embodiment, the methods of this invention are used to treat endocarditis caused by *Staphylococcus aureus*. In this embodiment, telavancin will typically be dosed daily for about 4 to about 6 weeks, or until the endocarditis has been treated.

In another embodiment, the methods of this invention are used to treat osteomyelitis caused by *Staphylococcus aureus*. In this embodiment, telavancin will typically be dosed daily for about 4 to about 8 weeks, or until the osteomyelitis has been treated. In one embodiment, treatment is for at least 6 weeks.

In another embodiment, the methods of this invention are used to treat a prosthetic joint infection (PJI) caused by *Staphylococcus aureus*. In this embodiment, telavancin will typically be dosed daily for about 2 to about 8 weeks, including about 4 to about 6 weeks, or until the osteomyelitis has been treated. In one embodiment, treatment is for at least 6 weeks.

In another embodiment, the methods of this invention are used to treat a complicated skin and skin structure infection caused by *Staphylococcus aureus*. In this embodiment, telavancin will typically be dosed daily for about 7 to about 14 days, or until the complicated skin and skin structure infection has been treated.

The methods of the present invention can be used to treat infections caused by methicillin-susceptible *Staphylococcus aureus* and methicillin-resistant *Staphylococcus aureus*. Identification of *Staphylococcus aureus*, including the particular strain of *Staphylococcus aureus*, as the causative agent of an infection can be achieved using conventional diagnostic tests, including rapid diagnostic tests. For example, *Staphylococcus aureus* bacteremia can be identified using a blood culture test, *Staphylococcus aureus* pneumonia can be identified using a sputum, blood or pleural fluid culture, and a *Staphylococcus aureus* complicated skin and skin structure infection can be identified using a skin, wound or fluid sample from the site of the infection.

Use of a daily dosing regimen of the present invention to treat infections caused by *Staphylococcus aureus* is expected to provide a similar clinical response at test of cure (TOC) relative to the prior dosing regimen with a predicted reduction in the risk of AKI and a predicted reduction in 28-day-all-cause mortality as described in the following Examples.

EXAMPLES

The following examples are provided to illustrate various representative embodiments and aspects of this invention and are not intended to limit the scope of this invention unless specifically indicated.

The following abbreviations are used herein:

| Abbreviation | Definition |
| --- | --- |
| ε (ERR) | Independent normally distributed random effects with mean zero and variance $\sigma^2$ |
| θ (THETA) | Typical (population) value of a pharmacokinetic parameter (theta) |
| $\sigma^2$ | Variance of intra-individual error (ε) |
| $\omega^2$ | Variance of inter-individual error (η) |
| η (ETA) | Independent normally distributed random effects with mean zero and variance $\omega^2$ |
| AUC | Area under the concentration-time curve |
| BLQ | Below the limit of quantitation for the bioanalytical assay |
| BMI | Body mass index (kg/m$^2$) |
| CI | Confidence interval |
| CL | Clearance (L/hr) |
| Cl/F | Oral clearance (L/h) |
| CrCl | Creatinine clearance (mL/min) |
| cm | Centimeter(s) |
| $C_{max}$ | Maximum observed concentration |
| CWRES | Conditional weighted residuals |
| DV | Dependent variable (observed concentration) |
| F | Bioavailability fraction |
| FOCE INTER | First order conditional estimation with interaction |
| g | Gram(s) |
| hr | Hour |
| HT | Height in cm |
| in | Inch(es) |
| IPRED | Predicted values for the individual |
| KA | Absorption rate constant (per h) |
| Ke | Elimination rate constant (per h) |
| kg | Kilogram(s) |
| L | Liter |
| LLOQ | Lower limit of quantitation |
| LOESS | Local regression |
| MDV | Missing dependent variable (concentration) |
| min | Minute |
| mL | Milliliter |
| mg | Milligram(s |
| NONMEM | Nonlinear mixed effects modeling software |
| PK | Pharmacokinetic |
| PRED | Predicted values for the population |
| PRED | Predicted values for the population |
| Q/F | Intercompartmental clearance |
| R | Software program for data handling, plotting and modeling |

| Abbreviation | Definition |
| --- | --- |
| RES | Residuals; differences between observed and predicted values |
| RSE | Relative standard error |
| SD | Standard deviation |
| SE | Standard error |
| SeCr | Serum creatinine (mg/dL) |
| $t_{1/2}$ | Half-life (hours) |
| Vc/F | Volume of distribution of the central compartment |
| Vp/F | Volume of distribution of the peripheral compartment |
| WRES | Weighted residuals |
| WHO | World Health Organization |
| WT | Weight in kg |

Other abbreviations used herein have their standard meanings unless otherwise indicated.

Example 1

Simulations of Pharmacokinetic Exposure to Telavancin in Subjects with the Prior Dosing Regimen and a New Dosing Regimen 1.1 Summary The objective of this analysis was to estimate the exposure to telavancin from the prior dosing regimen (10 mg/kg QD) and a new dosing regimen (7.5 mg/kg QD) in subjects with normal renal function and various stages of renal impairment. Exposures from a QD dose for subjects with CrCl<30 mL/min, a dose reduction of 25% (relative to the prior 10 mg/kg dose) and a maximum dose cap of 750 mg (or 562 mg for those with moderate renal impairment or 375 mg for those with severe renal impairment) for subjects exceeding 100 kg were compared to estimated exposures from the prior doses, e.g., the doses recommended in VIBATIV® (telavancin) Prescribing Information; Revised March 2014.

Exposures were based on 100 simulated clinical trials using the all-treated telavancin population (n=1771 subjects) from the existing Phase III HAP (n=750) and cSSSI (n=1021) study data and demographics.

In this analysis, the new dosing regimen maintains a comparable range of exposures for all subjects with a predicted 23% reduction in 28-day-all-cause mortality, a 37% reduction in the risk of AKI, and a predicted similar clinical response at TOC relative to the prior 10 mg/kg QD dose.

1.2 Introduction

Telavancin is a concentration dependent, rapidly bactericidal, injectable antibiotic with activity against clinically important Gram positive pathogens. The drug is approved in the US for treatment of complicated skin and skin structure infections (cSSSI) and hospital acquired bacterial pneumonia/ventilator acquired bacterial pneumonia (HABP/VABP) in adults.

Exposures for a new dosing regimen for telavancin were estimated using a population PK model developed from Phase 1, 2 and 3 clinical studies. Alterations in the dosing regimen from the prior dosing regimen were: (1) dose reduced by 25% in all subjects, (2) maximum dose limited to the dose administered for subjects at 100 kg and (3) halve the dose and increase dose frequency to QD for subjects with CrCl<30 mL/min.

Telavancin is primarily cleared via the kidneys and is dosed based on weight. The prior telavancin dosing regimen adjusts the dose in renally impaired subjects to maintain comparable exposures. No additional dose adjustments are recommended for obesity, but population PK analysis has predicted that subjects with increased BMI have higher exposures (see Example 2).

Prospective analysis of telavancin Phase 3 data has suggested increased exposures are associated with an increased probability of AKI in all subjects, and an increased likelihood of mortality in HABP/VABP subjects with renal impairment (see Example 3). No relationship was identified between exposure and efficacy (e.g., clinical response at test of cure).

A new dosing regimen was evaluated in simulated patients that aimed to optimize exposures in all subjects and maintain comparable exposures in subjects with increased weight or decreased renal function relative to patients with normal weight and/or normal renal function. Telavancin exposures for this new dosing regimen were estimated by generating a virtual population of HABP/VABP and cSSSI subjects (n=1771) using the demographics of the all-treated population in the Phase 3 trials. Steady-state exposures were estimated based on a total of 100 simulations following the administration of telavancin. The predicted likelihood of mortality, AKI and efficacy for each simulation was estimated using a logistic regression model of exposure and outcomes.

1.3 Objectives

The objectives of the population pharmacokinetic analysis included:

(a) Compare the exposure of telavancin administered using the prior dosing regimen (10 mg/kg QD) and the new dosing regimen (7.5 mg QD) over a range of weights and renal function by simulating exposures using a population PK model;

(b) Compare the exposure of telavancin administered using the prior dosing regimen (10 mg/kg QD) and the new dosing regimen (7.5 mg/kg QD) in a subpopulation of subjects with higher exposures (obese subjects with impaired renal function and in HABP/VABP subjects with impaired renal function);

(c) Estimate the likelihood of mortality, AKI and cure for the prior and new dosing regimens using a logistic model of exposure vs. outcomes; and (d) Estimate the likelihood of mortality, AKI and cure for the prior and new dosing regimens using a logistic model of exposure vs. outcomes in various sub-populations of interest (underweight subjects, obese subjects with impaired renal function and HABP/VABP subjects with impaired renal function.

1.4 Analysis Assumptions

The assumptions underlying this analysis were as follows:

(a) A hierarchical (population) model can account for the two levels of variability inherent in repeated measurement designs—inter-individual and intra-individual variability;

(b) The pharmacokinetic parameters are log-normally distributed;

(c) The random effects describing inter-individual variability ($\eta_{ij}$) in pharmacokinetic parameters are independent, normally distributed with mean zero and a variance $\omega^2$; and (d) The random effects describing intra-individual variability or residual error ($\varepsilon_{ij}$) are independent, normally distributed with mean zero and a variance $\sigma^2$.

1.5 Methods 1.5.1 Software and Platform

Data management and calculation of simulated exposures were carried out using R version 3.0.2 (The R project for Statistical Computing, http://www.r-project.org). PK predictions were generated using NONMEM version 7.2 (ICON plc, Dublin, Ireland) on a Windows 7 platform with the gfortran compiler version 4.6.0.

1.5.2 Telavancin Population PK Model

A population PK model for telavancin was developed using the combined datasets from Phase 1, 2 and Phase 3 HABP/VABP and cSSSI studies where plasma concentrations of telavancin were assayed in patients. Data was collated from 1346 subjects, 863 males and 483 females (7262 plasma samples) ranging in age from 18 to 100, with measured body weights between 33.6 to 314 kg, calculated BMI between 12.3 and 94 kg/m², and creatinine clearances (Cockcroft-Gault at screening using ideal body weight) between 3 and 150 mL/min. The model provided the following:

| Pharmacokinetic parameter | Combined model |
|---|---|
| CL, liters/h | $1.15 \cdot (CrCl/99)^{0.454} \cdot (AGE/46)^{0.173} \cdot (WT/77)^{0.352} \cdot$ GEND $\cdot$ CSSSI1 |
| $V_1$, liters | $6.11 \cdot (CrCl/99)^{-0.214} \cdot (AGE/46)^{0.229} \cdot (WT/77)^{0.847}$ |
| Q, liters/h | $4.72 \cdot (CrCl/99)^{0.211} \cdot$ CSSSI2 |
| $V_2$, liters | $6.46 \cdot (CrCl/99)^{0.127} \cdot (AGE/46)^{0.381} \cdot (WT/77)^{0.548} \cdot$ CSSSI3 |

GEND = 1 for males, 0.933 for females
CSSSI1 = 1 for uninfected or HAP, 0.946 for cSSSI subject
CSSSI2 = 1 for uninfected or HAP, 1.62 for cSSSI subject
CSSSI3 = 1 for uninfected, 1.14 for cSSSI subject

| Model | OFV | Population estimate ± SE | Between subject variability (%) |
|---|---|---|---|
| Final Model | 34523.584 | | |
| CL (L/hr) | | 1.15 ± 0.04 | 29.8 |
| V1 (L) | | 6.11 ± 0.23 | 42.1 |
| Q (L/hr) | | 4.72 ± 0.34 | 38.1 |
| V2 (L) | | 6.46 ± 0.22 | 29.5 |
| Residual variability | | | |
| Proportional error | | 17% | |
| Additive error | | 0.36 µg/mL | |

1.5.3 Simulation of Telavancin Exposures in Phase 3 All-Treated Subjects

Telavancin PK profiles were simulated for each Phase 3 subject using the estimated PK parameters, inter-individual and residual variability determined during the population PK analysis based on the administered dose as recorded in the dataset. The individually estimated PK parameters were determined based upon the specific inter-individual errors for each subject determined using nonlinear mixed effect analysis.

The exposure for the new dosing regimen was simulated by 1) reducing the AMT and RATE (dosage amount and dosing rate) in the NONMEM datafile by 25%, 2) reducing the AMT and RATE by an additional 50% in subjects dosed Q48h (CrCl<30 mL/min) and reducing the II (dosing interval) to 24 hours and 3) recalculating the AMT and RATE by multiplying the recorded DOSE (in mg/kg) by 100 for subjects with weight >100 kg. 100 simulations were performed for each dataset of 1771 subjects using the SIMULATE command in NONMEM. Steady state plasma concentrations at 0, 0.5, 1, 1.5, 2, 3, 4, 5, 6, 8, 12, 18, 24, 36 and 48 hours after the infusion of telavancin were simulated for each subject using the prior and new regimens, with exposure over 24 hours calculated using the linear trapezoidal method.

1.5.4 Comparison of Simulated Exposures to Telavancin $AUC_{0-24h}$ values for the prior dosing regimen and the new dosing regimen were compared by determining the fraction of simulated subjects with exposures above a cutpoint of 767 µg·hr/mL (based on classification and regression tree analysis), and the fraction of subjects with exposures below 219 µg·hr/mL (based on a target attainment ratio of 219 and a MIC100 of 1 µg/mL). Values were determined for each simulated clinical trial (n=100), and presented as a mean and standard deviation.

A statistical model of the relationship between exposure and outcome determined using logistic regression analysis (see Example 3) was used to calculate the probability of mortality, AKI or cure for each simulated subject based on their exposure. The estimated fitted parameters for the logit function for each relationship between exposure and outcome was used, irrespective of statistical significance. The mean values for each outcome were calculated for each simulated trial (n=100) for the prior and new dosing regimens.

The relative risk (RR) for each outcome between the new dosing regimen relative to the prior dosing regimen was calculated for each simulated trial using the mean probability for each outcome.

$$\text{Relative risk} = \frac{p(event_{alternative})}{p(event_{current})}$$

The process was repeated for HABP/VABP subjects with renal impairment (CrCl≤50 mL/min).

The number of subjects needed to treat (NNT), i.e. the number of additional subjects treated with the new regimen required to spare one subject a change in outcome (death, AKI, reduced cure) was calculated for each simulated trial.

$$NNT = \frac{1}{p(event_{current}) - p(event_{alternative})}$$

The mean and standard deviation values for each outcome were calculated for all simulated clinical trials to evaluate the effect of variability in exposure on the number needed to treat.

1.5.6 Prior Dosing Guidelines for Telavancin

For subjects with normal renal function, the prior dosing guidelines state that telavancin should be administered IV at a dose of 10 mg/kg, in either 5% dextrose injection (D5W), sterile water for injection, or 0.9% sodium chloride; in 100 to 250 mL over 60 minutes, once every 24 hours. A dosage adjustment is required for subjects whose creatinine clearance is ≤50 mL/min, as listed in Table 1-1.

TABLE 1-1

Prior Telavancin Dosage Adjustment in Subjects with Renal Impairment

| Creatinine Clearance[a] (mL/min) | Telavancin Dosage Regimen |
|---|---|
| >50 | 10 mg/kg every 24 hours |
| 30-50 | 7.5 mg/kg every 24 hours |
| <30 | 10 mg/kg every 48 hours |

[a]Calculate using the Cockcroft-Gault formula and ideal body weight (IBW). Use actual body weight if it is less than IBW 1.5.7 New Dosing Guidelines for Telavancin For subjects with normal renal function, the new dosing guidelines of this example provide that telavancin should be administered IV at a dose of 7.5 mg/kg, in e.g., either 5% dextrose injection (D5W), sterile water for injection, or 0.9% sodium chloride; in 100 to 250 mL over 60 minutes, once every 24 hours. The daily telavancin dose should not exceed the dose at 100 kg for any patient weighing more than 100 kg (750 mg, 562 mg or 375 mg). A dosage adjustment is required for subjects whose creatinine clearance is ≤50 mL/min, as listed in Table 1-2.

TABLE 1-2

Telavancin Dosage Adjustment in Subjects with Renal Impairment for New Dosing Regimen

| Creatinine Clearance[a] (mL/min) | Telavancin Dosage Regimen | Maximum Dose |
|---|---|---|
| >50 | 7.5 mg/kg every 24 hours | 750 mg |
| 30-50 | 5.625 mg/kg every 24 hours | 562 mg |
| <30 | 3.75 mg/kg every 24 hours | 375 mg |

[a]Calculate using the Cockcroft-Gault formula and ideal body weight (IBW). Use actual body weight if it is less than IBW 1.6 Results 1.6.1 Data The data for the simulations was based on 1771 subjects from Studies 0015, 0017, 0018 and 0019. One subject (0018-38160-2518) did not have a recorded value for baseline CrCl and was removed from the simulation. One subject (0015-06013-4221) did not have a recorded value for weight and was removed from the simulation. The population consisted of 750 HABP/VABP subjects and 1021 cSSSI subjects, 706 females and 1065 males, ranging in age from 18 to 100 with measured body weights from 30 to 314 kg, calculated BMI between 11 and 94 kg/m², and creatinine clearances (Cockcroft-Gault at screening) between 5 and 369 mL/min (Table 1-3).

TABLE 1-3

Demographics of Simulated Population

| | mean ± SD (range) | | |
|---|---|---|---|
| | HABP/VABP | cSSSI | Total |
| n | 750 | 1021 | 1771 |
| AGE (years) | 62 ± 19 (18, 100) | 49 ± 16 (18, 96) | 54 ± 18 (18, 100) |
| WEIGHT (kg) | 72 ± 21 (30, 226) | 86 ± 27 (39, 314) | 80 ± 26 (30, 314) |
| HEIGHT (cm) | 168 ± 10 (122, 198) | 170 ± 10 (127, 201) | 169 ± 10 (122, 201) |
| BMI (kg/m²) | 26 ± 7 (11, 88) | 30 ± 9 (13, 94) | 28.0 ± 8.3 (11, 94) |
| CrCl (mL/min) | 84 ± 57 (5, 369) | 95 ± 39 (6, 298) | 91 ± 47 (5, 369) |
| SEX | F = 261, M = 489 | F = 445, M = 576 | F = 706, M = 1065 |

TABLE 1-3-continued

Demographics of Simulated Population mean ± SD (range)

|  | HABP/VABP | cSSSI | Total |
|---|---|---|---|
| n | 750 | 1021 | 1771 |
| MORTALITY | Y = 178, N = 572, | Y = 9, N = 1012, | Y = 187, N = 1584 |
| AKI | Y = 171, N = 542, UNKNOWN = 37 | Y = 120, N = 871, UNKNOWN = 30 | Y = 291, N = 1413, UNKNOWN = 67 |
| CURE | CURE = 442, INDETERMINATE = 96, NOT CURED = 0, FAILURE = 99, UNKNOWN = 113 | CURE = 788, INDETERMINATE = 46, NOT CURED = 123, FAILURE = 0, UNKNOWN = 64 | CURE = 1230, INDETERMINATE = 142, NOT CURED = 123, FAILURE = 99, UNKNOWN = 177 |

The majority of the subjects had normal renal function (CrCl>80 mL/min) and weighed between 60 and 105 kg (Table 1-4).

TABLE 1-4

Number of Subjects as Defined by Weight and Renal Function among the HABP/VABP and cSSSI Phase 3 Population

| N = 1771 | <30 mL/min | 30-50 mL/min | 50-80 mL/min | 80-150 mL/min | >150 mL/min |
|---|---|---|---|---|---|
| <60 kg | 39 | 64 | 79 | 92 | 24 |
| 60-105 kg | 93 | 139 | 264 | 597 | 129 |
| 105-150 kg | 11 | 14 | 56 | 116 | 21 |
| >105 kg | 3 | 4 | 8 | 17 | 1 |

1.6.2 Simulated Exposure to Telavancin Based Upon Prior Dosing Regimen

Figure 2:
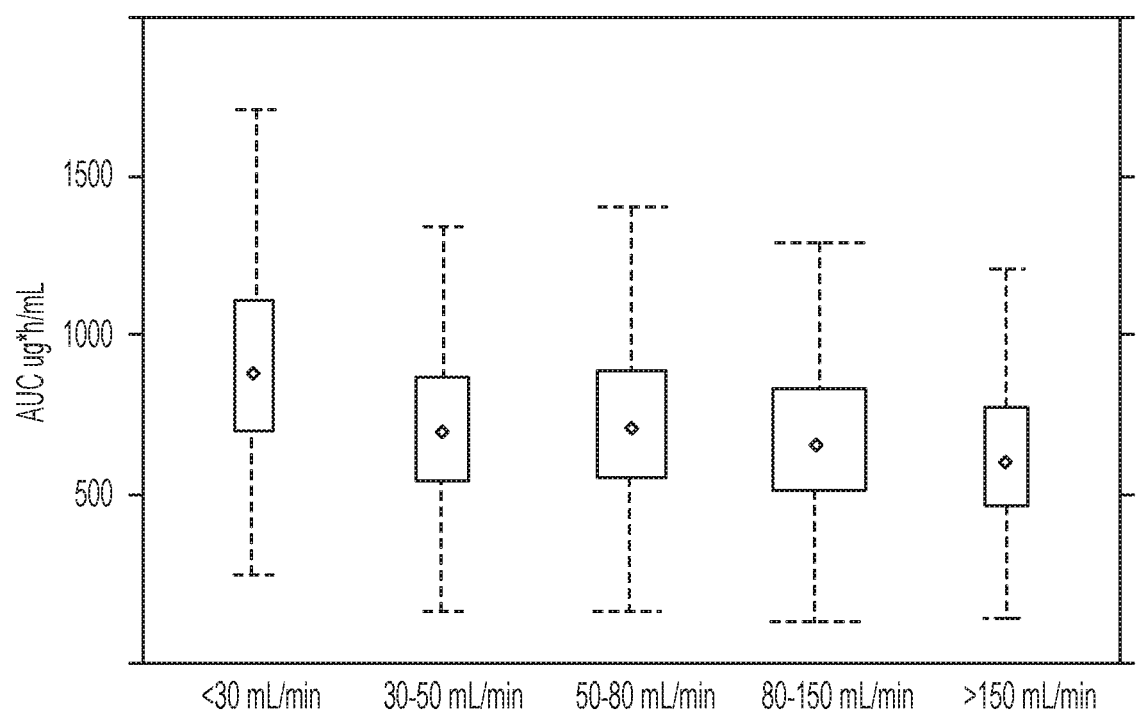
FIG. 2 shows the predicted $AUC_{0-24h}$ of the prior dosing regimen as a function of renal impairment.
Figure 3A:
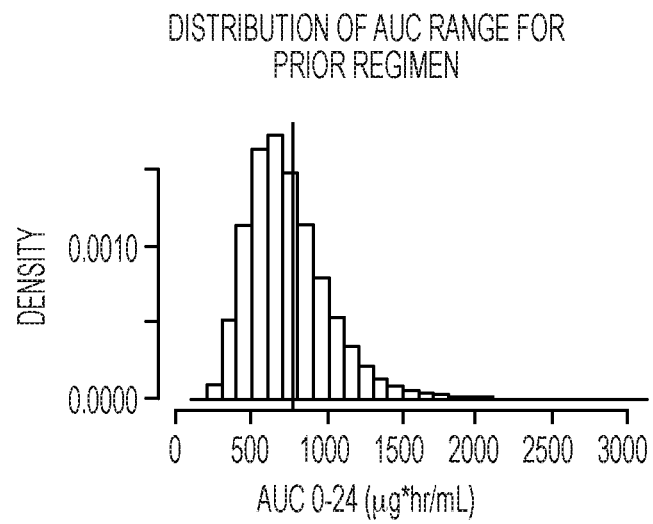
FIG. 3A shows the distribution of predicted $AUC_{0-24h}$ values for all cSSSI and HABP/VABP subjects dosed with the prior dosing regimen.
Figure 3B:
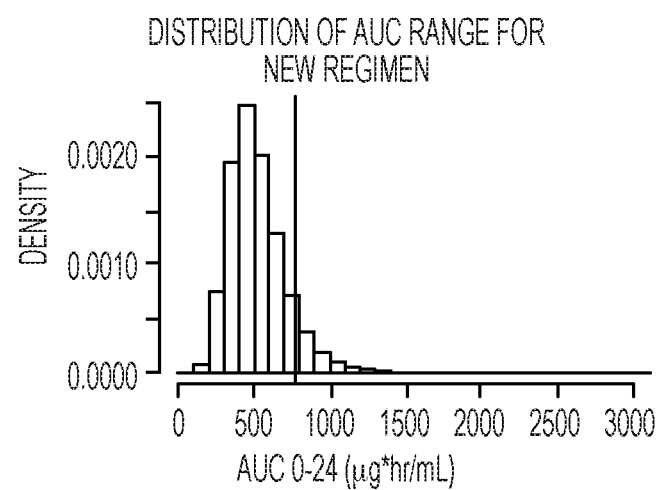
FIG. 3B shows the distribution of predicted $AUC_{0-24h}$ values for all cSSSI and HABP/VABP subjects dosed with a new dosing regimen of the present invention.

Simulated exposures to telavancin increase with increasing body weight (FIG. 1). In subjects with CrCl between 30 and 50 mL/min, the prior dose adjustment for renal impairment maintains exposure similar to the exposure in subjects with normal renal function (FIG. 2). However, for subjects with CrCl<30 mL/min, the dose of 10 mg/kg Q48h results in higher exposures to telavancin during the first 24 hours of dosing compared to the second day. Subjects with CrCl>150 mL/min had simulated exposures that were comparable to subjects with CrCl between 80 and 150 mL/min. FIG. 3A shows the cumulative distribution of $AUC_{0-24h}$ and $C_{min}$ for the prior dosing regimen.

1.6.3 Simulated Exposure to Telavancin Based Upon New Dosing Regimen

Figure 5A:
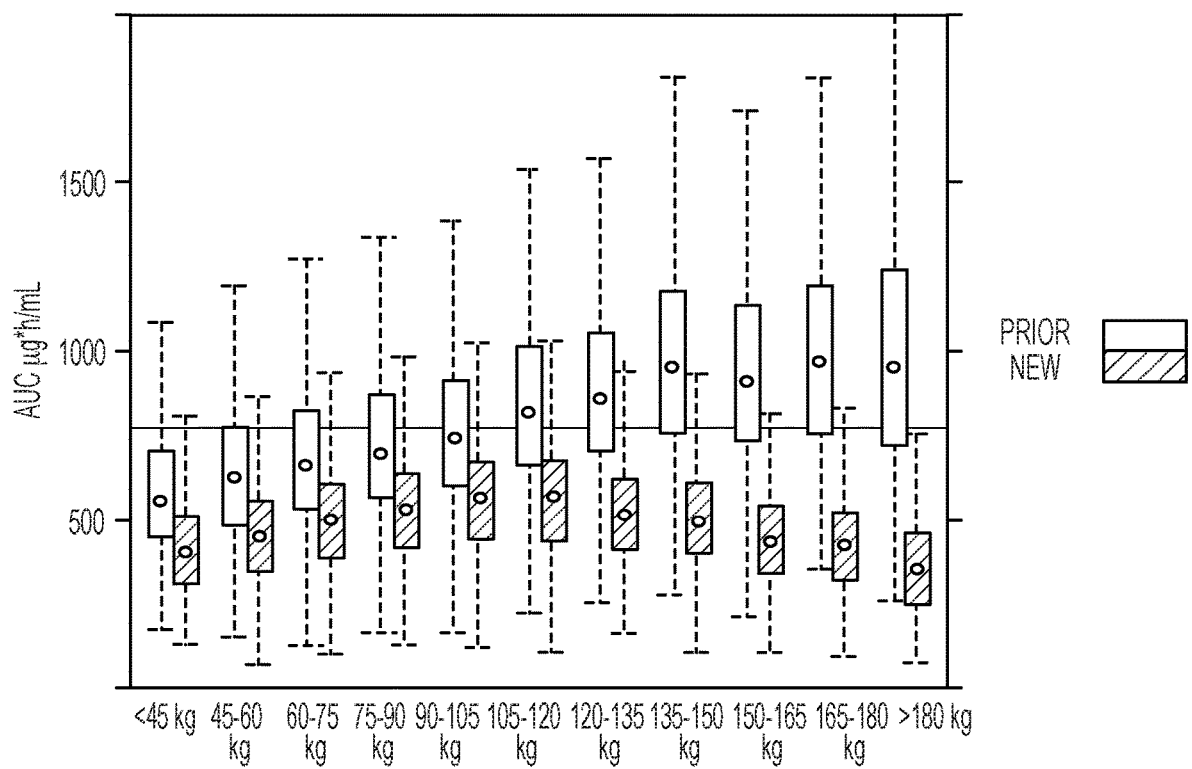
FIG. 5A shows a comparison of predicted exposures (AUC) for various subject weight ranges for the prior dosing regimen and a new dosing regimen of the present invention.
Figure 5B:
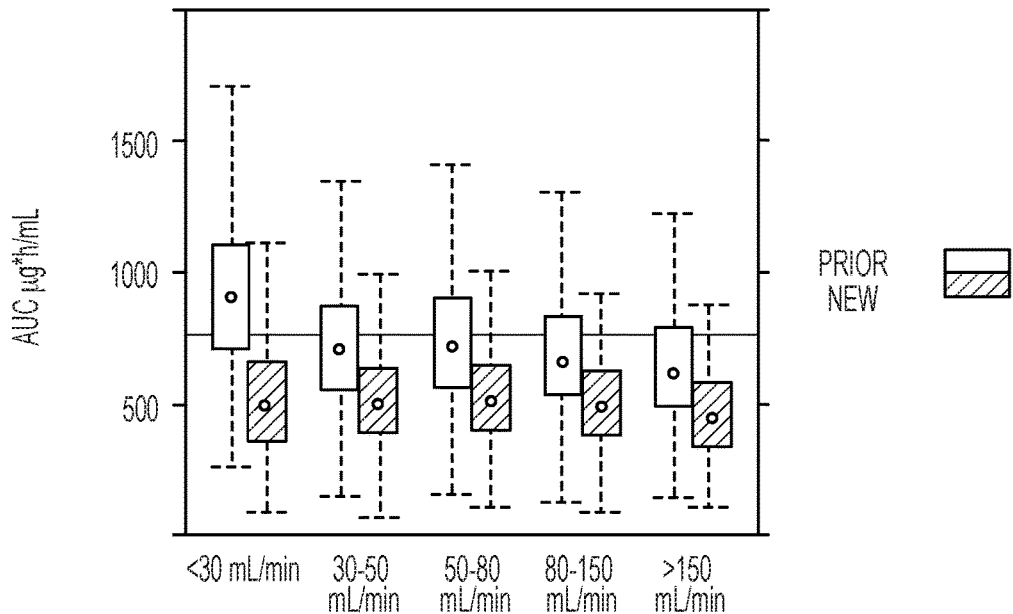
FIG. 5B shows a comparison of predicted exposures (AUC) for various subject renal function ranges for the prior dosing regimen and a new dosing regimen of the present invention.
Figure 6A:
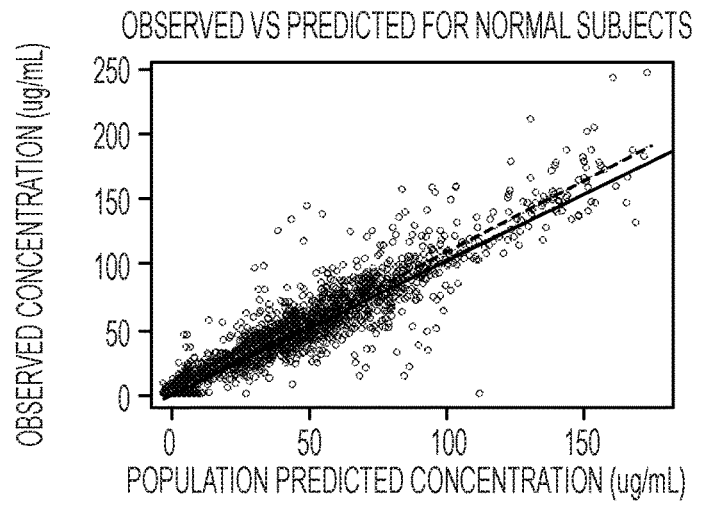
FIG. 6A shows the observed versus predicted telavancin concentrations for normal subjects.
Figure 6B:
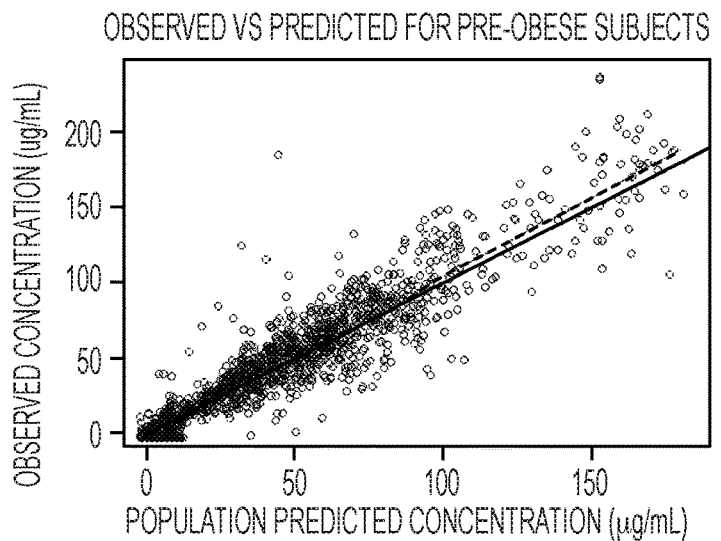
FIG. 6B shows the observed versus predicted telavancin concentrations for pre-obese subjects.
Figure 6C:
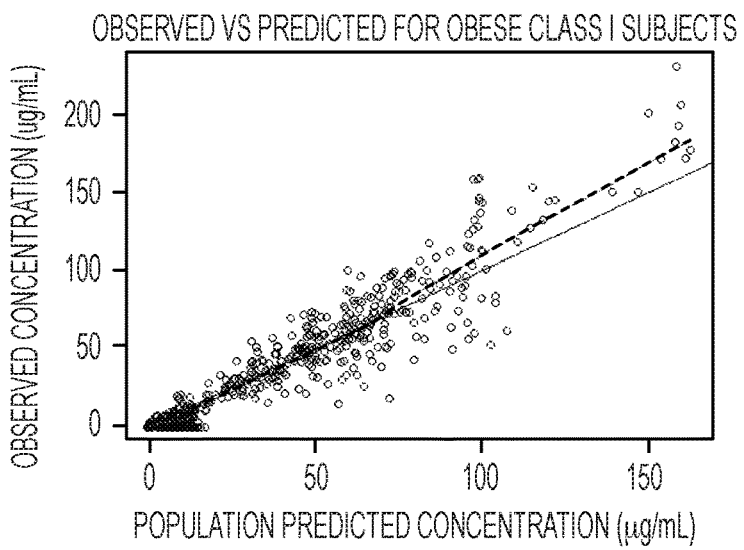
FIG. 6C shows the observed versus predicted telavancin concentrations for obese Class I subjects.
Figure 6D:
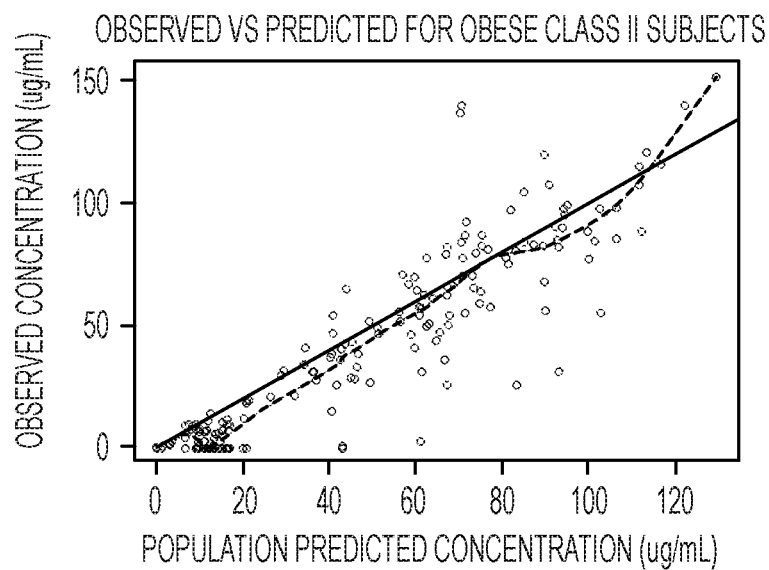
FIG. 6D shows the observed versus predicted telavancin concentrations for obese Class II subjects.
Figure 6E:
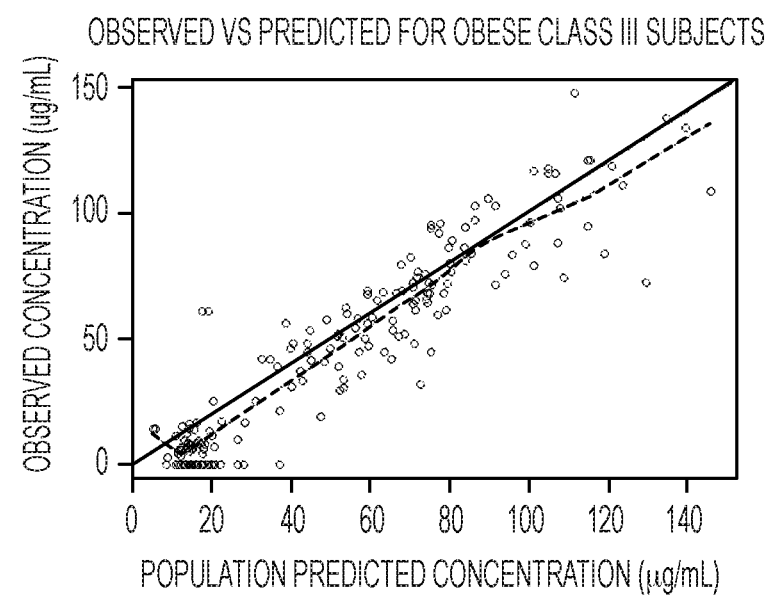
FIG. 6E shows the observed versus predicted telavancin concentrations for obese Class III subjects.
Figure 7A:
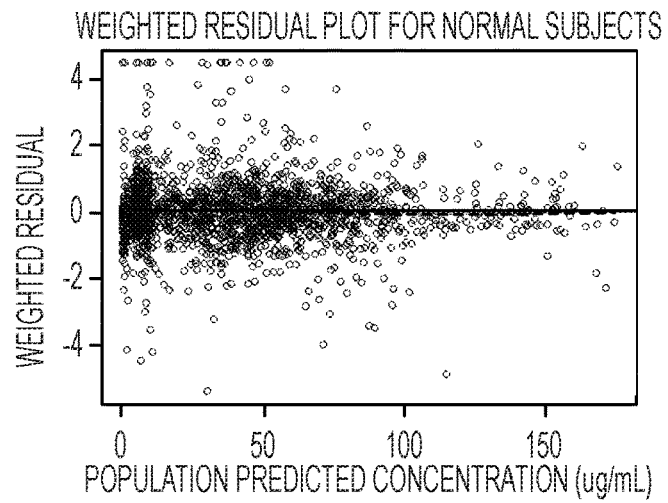
FIG. 7A shows the weighted residual versus population predicted telavancin concentrations for normal subjects.
Figure 7B:
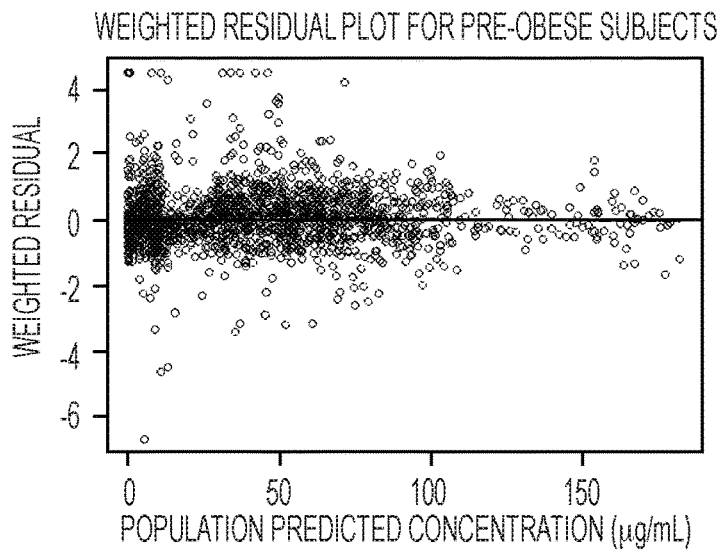
FIG. 7B shows the weighted residual versus population predicted telavancin concentrations for pre-obese subjects.
Figure 7C:
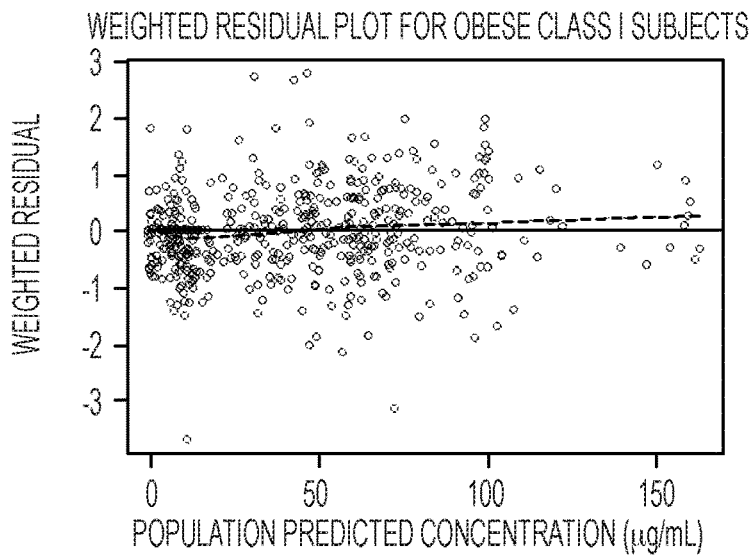
FIG. 7C shows the weighted residual versus population predicted telavancin concentrations for Class I obese subjects.
Figure 7D:
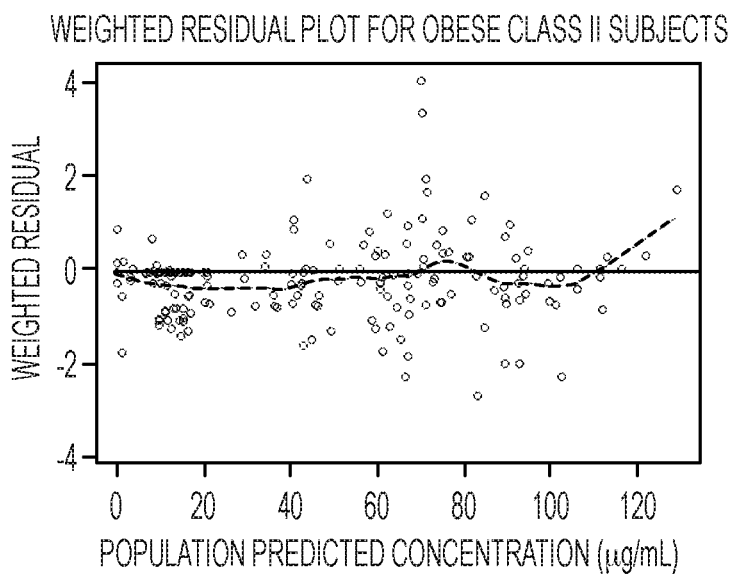
FIG. 7D shows the weighted residual versus population predicted telavancin concentrations for Class II obese subjects.
Figure 7E:
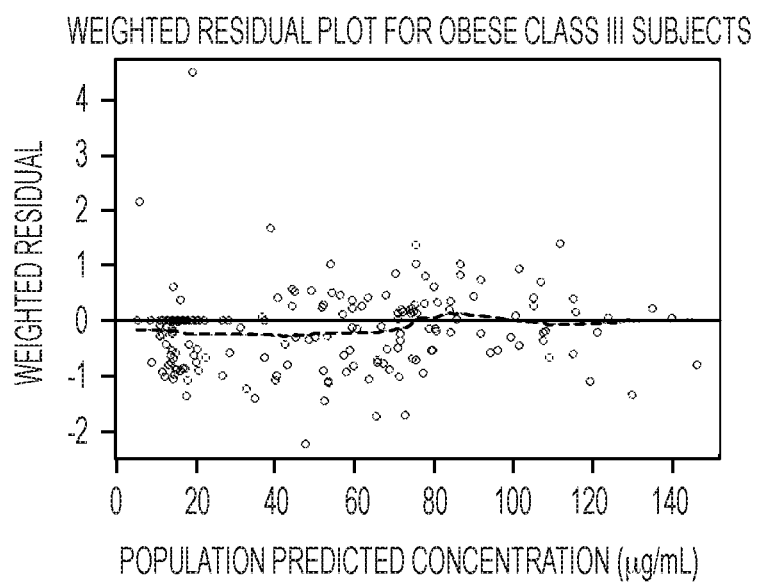
FIG. 7E shows the weighted residual versus population predicted telavancin concentrations for Class III obese subjects.

A 25% decrease in the dose of telavancin was predicted to reduce the exposure by 25% in all subjects compared to the prior dosing regimen (FIG. 5A and FIG. 5B). The change from Q48h dosing to Q24 dosing at half the dose for subjects with CrCl<30 mL/min halves the exposure over the first 24 hours. A cap for doses in subjects above 100 kg is anticipated to limit exposure increases for subjects with weights greater than 100 kg. The mean fraction of subjects with an exposure greater than 767 μg·hr/mL was reduced from 39% to 10%, whilst the mean number of subjects in each trial with an exposure less than 219 μg·hr/mL was increased from 0% to 1.3% (Table 1-5). The lower threshold of 219 μg·hr/mL was chosen based upon the $AUC_{24}$/MIC ratio of 219 which was identified as the exposure target associated with a 1-log reduction in colony counts from baseline for MRSA in the neutropenic murine-thigh infection model studies (see, Hegde S S et al., 2004. Pharmacodynamics of telavancin (TD-6424), a novel bactericidal agent, against gram-positive bacteria. *Antimicrob. Agents Chemother.* 48:3043-3050), and assuming an upper bound MIC of 1 μg/mL.

TABLE 1-5

Fraction of Simulated Subjects Above an $AUC_{0-24\ h}$ Cutpoint of 767 μg · hr/mL and Below an AUC/MIC Cutpoint of 219 μg · hr/mL

| % of subjects with | Dosing regimen | |
|---|---|---|
| $AUC_{0-24\ h}$: | 10 mg/kg QD[1] | 7.5 mg/kg QD[2] |
| >767 μg*hr/mL | 39 ± 1.2% | 10 ± 0.6% |
| <219 μg*hr/mL | 0.1 ± 0.1% | 1.3 ± 0.3% |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

1.6.4 Exposure in Underweight, Obese cSSSI and Renally Impaired HABP/VABP Populations In underweight subjects (weight ≤45 kg, n=48), the new dosing regimen is predicted to reduce exposure compared to the prior dosing regimen (FIG. 5A). The mean fraction of underweight subjects with an exposure greater than 767 μg·hr/mL was reduced from 16% to 3%, whilst the mean number of subjects in each trial with an exposure less than 219 μg·hr/mL was increased from 0.4% to 5.1% (Table 1-6).

TABLE 1-6

Fraction of Simulated Subjects with Weight ≤45 kg Above an $AUC_{0-24\ h}$ Cutpoint of 767 μg · hr/mL and Below an AUC/MIC Cutpoint of 219 μg · hr/mL

| % of Subjects with | Dosing regimen | |
|---|---|---|
| $AUC_{0-24\ h}$: | 10 mg/kg QD[1] | 7.5 mg/kg QD[2] |
| >767 μg*hr/mL | 16 ± 4.2% | 3.4 ± 2.3% |
| <219 μg*hr/mL | 0.4 ± 0.9% | 5.1 ± 2.8% |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

Figure 4A:
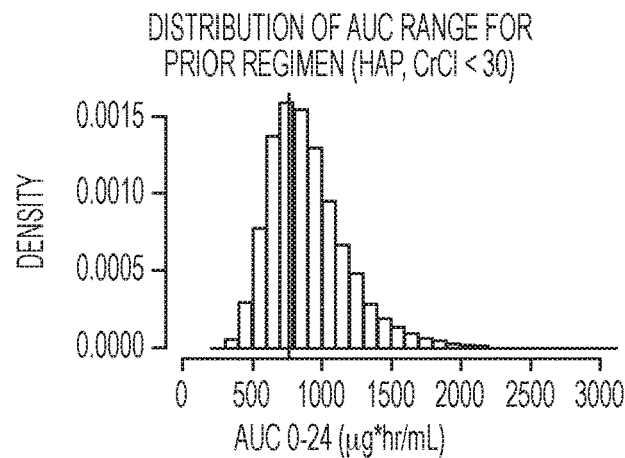
FIG. 4A shows the distribution of the predicted $AUC_{0-24h}$ values for HABP/VABP subjects with a CrCl<30 mL/min with the prior dosing regimen (10 mg/kg Q48h).
Figure 4B:
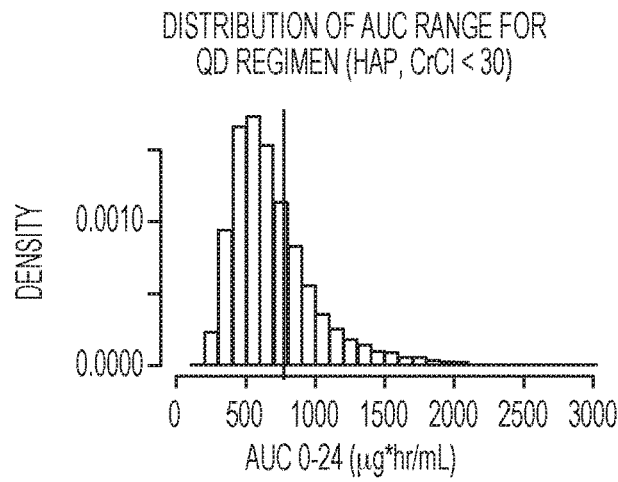
FIG. 4B shows the distribution of the predicted $AUC_{0-24h}$ values for HABP/VABP subjects with a CrCl<30 mL/min with a daily dosing regimen (5 mg/kg QD).

In HABP/VABP subjects with severe renal impairment (CrCl<30 mL/min, n=98), modifying the regimen to 5 mg/kg once daily is anticipated to reduce the fraction of subjects with an $AUC_{0-24h}$>767 μg·hr/mL from 64% to 31% (FIG. 4B). The new dosing regimen includes a 25% reduction and daily dosing and employing a maximum daily dose of 375 mg in subjects weighing greater than 100 kg. These modifications are anticipated to reduce the fraction of subjects with an $AUC_{0-24h}$>767 μg·hr/mL from 64% to 13%

Figure 4C:
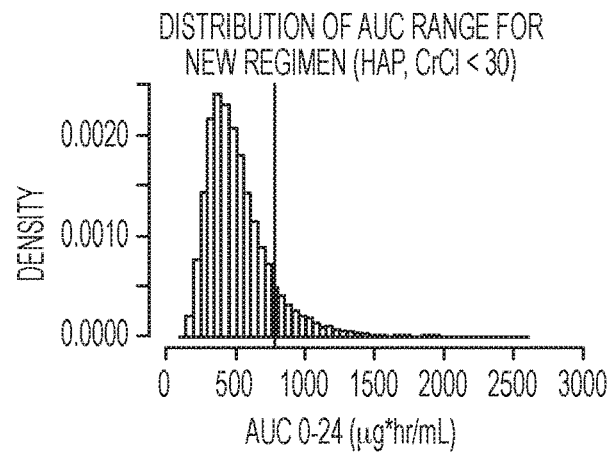
FIG. 4C shows the distribution of the predicted $AUC_{0-24h}$ values for HABP/VABP subjects with a CrCl<30 mL/min with a new dosing regimen (3.75 mg/kg QD with a maximum dose of 375 mg for subjects >100 kg) of the present invention.

(FIG. 4C), whilst the mean number of subjects in each trial with an exposure less than 219 µg·hr/mL was increased from 0% to 2.1% (Table 1-7).

TABLE 1-7

Fraction of Simulated HABP/VABP Subjects with CrCl <30 mL/min Above an $AUC_{0-24\ h}$ Cutpoint of 767 µg · hr/mL and Below an AUC/MIC Cutpoint of 219 µg · hr/mL

| % of Subjects with | Dosing regimen | |
|---|---|---|
| $AUC_{0-24\ h}$: | 10 mg/kg QD[1] | 7.5 mg/kg QD[2] |
| >767 µg*hr/mL | 64 ± 4.1% | 13 ± 2.6% |
| <219 µg*hr/mL | 0.0 ± 0.0% | 2.1 ± 1.4% |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

1.6.5 Comparison of the Predicted Effect on Outcomes between Prior and New Dosing Regimen Table 1-8 describes the probability for each tested outcome for the prior and new dosing regimen based on the logistic regression model (see Example 3). The new dosing regimen is predicted to have a 23% reduction in the risk of mortality, a predicted 37% reduction in the risk of AKI and a similar likelihood of clinical response at TOC relative to the prior 10 mg/kg QD dosing regimen

TABLE 1-8

Risks for Prior Dosing Regimen and New Dosing Regimen in All Subjects

| | Dosing Regimen | | Risk Ratio |
|---|---|---|---|
| Incidence % | 10 mg/kg QD[1] | 7.5 mg/kg QD[2] | (95% CI) |
| Mortality | 8.7 | 6.7 | 0.77 (0.61, 0.97) |
| AKI | 15.7 | 10.1 | 0.65 (0.54, 0.77) |
| Clinical Response at TOC | 78.0 | 76.4 | 0.98 (0.95, 1.02) |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

Table 1-9 describes the probability for each tested outcome for the prior and new dosing regimen based on the logistic regression model in HABP/VABP subjects with CrCl≤50 mL/min. The likelihood of 28-day all-cause mortality and AKI are reduced (49% and 22%, respectively) whilst the likelihood of clinical response at TOC is similar to the prior 10 mg/kg QD dosing regimen.

TABLE 1-9

Risks for Prior Dosing Regimen and New Dosing Regimen in HABP/VABP Subjects with CrCl ≤50 mL/min

| | Dosing Regimen | | Risk Ratio |
|---|---|---|---|
| Incidence % | 10 mg/kg QD[1] | 7.5 mg/kg QD[2] | (95% CI) |
| Mortality | 43.3 | 21.9 | 0.51 (0.38, 0.67) |
| AKI | 21.0 | 16.4 | 0.78 (0.54, 1.14) |
| Clinical Response at TOC | 58.7 | 67.0 | 1.14 (1.00, 1.31) |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

Table 1-10 describes the probability for each tested outcome for the prior and new dosing regimen based on the logistic regression model in cSSSI subjects with weight >100 kg. The likelihood of AKI is reduced 71% and the likelihood of clinical response at TOC is similar to the prior 10 mg/kg QD dosing regimen.

TABLE 1-10

Risks for Prior Dosing Regimen and New Dosing Regimen in cSSSI Subjects with Weight >100 kg

| | Dose | | Risk Ratio |
|---|---|---|---|
| Incidence % | 10 mg/kg QD[1] | 7.5 mg/kg QD[2] | (95% CI) |
| AKI | 20.5 | 6.0 | 0.29 (0.17, 0.51) |
| Clinical Response at TOC | 85.4 | 88.2 | 1.03 (0.96, 1.11) |

[1]Dose is modified to 7.5 mg/kg QD for patients with CrCl between 30-50 mL/min and 10 mg/kg Q48 for patients with CrCl <30 mL/min
[2]Dose is modified to 5.625 mg/kg QD and 3.75 mg/kg QD in subjects with CrCl between 30-50 mL and <30 mL/min, respectively. A maximum dose of 750 mg (or 562 and 375 mg for patients with renal impairment) is employed for subjects weighing >100 kg.

1.7 Discussion

The objective of this analysis was to simulate the exposure of telavancin and the predicted effect on outcomes with a new dosing regimen. Simulated exposures for the new dosing regimen are based on the direct relationship between administered dose and exposure.

The new dosing regimen resulted in changes in the exposure for all subjects, with consistent exposures over a range of weights and renal functions. Morbidly obese and underweight subjects with healthy renal function are expected to have the lowest exposures to telavancin. Obese subjects with renal impairment are predicted to have lower exposures comparable to non-obese subjects with normal renal function based on the limited number of renally impaired obese subjects in the patient population (n=42).

The predicted effect on outcomes is based on the logistic regression analysis of observed exposures in all Phase 3 trials. The statistical model describing the relationship between exposure and AKI was statistically significant. The models describing the relationship between exposure and mortality/cure were not statistically significant. Based on these models, the predicted effect on reducing AKI was greater than the effect on mortality and cure.

HABP/VABP subjects with renal impairment (CrCl≤50 mL/min) were shown to have a significant relationship between exposure and mortality (see Example 3). In these subjects, the new dosing regimen results in a larger predicted reduction in mortality, and an increased likelihood of cure.

cSSSI subjects with weight >100 kg were shown to have a significant relationship between exposure and AKI (see Example 3). In these subjects, the new dosing regimen results in a larger predicted reduction in AKI, and an increased likelihood of cure.

1.8 Conclusion

Based on this analysis, a dose reduction of 25%, a maximum dose cap for subjects weighing greater than 100 kg and QD dosing for subjects with CrCl<30 mL/min is predicted to maintain a consistent range of exposures across the range of weights and renal function observed in the Phase 3 trials. The change in the dosing regimen is predicted to reduce the incidence of AKI, with smaller reductions in mortality and efficacy.

Rounding the doses to the nearest tenth of a milligram, the daily dose of telavancin suggested by this analysis for a patient based on the patient's body weight and creatinine clearance are as shown in Table I:

TABLE I

Dose of Telavancin Based on Creatinine Clearance and Body Weight

| Creatinine Clearance mL/min | Dose of Telavancin mg/kg | Not to Exceed mg/day |
|---|---|---|
| >50 | 7.5 | 750 |
| 30-50 | 5.6 | 560 |
| <30 | 3.8 | 380 |

Example 2

Simulated Telavancin Exposures in Obese Subjects Using a Population PK Model 2.1 Summary The objective of this analysis was to estimate the exposure of telavancin in obese subjects (based on World Health Organization (WHO) obesity classification) using a population PK model of telavancin. Body weight is a significant covariate on telavancin plasma clearance and volume of distribution in the population PK model (see, Samara et al. Population pharmacokinetics of telavancin in healthy subjects and patients with infections. *Antimicrobial Agents and Chemother.* 2012; 56(4):2067-73)). A simulated population of 20,000 normal and obese subjects (4,000 subjects for each obesity category of normal, pre-obese, obese class I, II and III) with normal renal function (CrCl>80 mL/min) and BMI ranging from 18.5 to 60 kg/m$^2$ was generated by sampling (with replacement) the demographic data from the existing Phase III HAP and cSSSI study data.

The exposure of telavancin in obese subjects between the ages of 18 and 60 with normal renal function (CrCl between 80 and 150 mL/min) is predicted to increase up to 43% in subjects in Obesity Class III (BMI≥40.0 kg/m$^2$) relative to normal subjects (BMI 18.5-24.9 kg/m$^2$).

2.2 Introduction

This analysis is designed to estimate the single-dose pharmacokinetics of telavancin in obese subjects. Exposures of telavancin in obese subjects were estimated using a population PK model of telavancin developed from Phase 1, 2 and 3 clinical studies. Subjects were classified according to the WHO obesity classification (Normal: 18.5-24.9, Pre-Obese 25.0-29.9, Obese Class I: 30.0-34.9, Obese Class II: 35.0-39.9, Obese Class III: ≥40.0).

Variability in the exposure to telavancin in obese subjects was estimated by generating a virtual population of obese subjects with BMI values from 18.5 to 45 kg/m$^2$ by generating 4,000 subjects from each WHO classification by sampling (with replacement) from the distribution of age, BMI and CrCl from the telavancin clinical PK population used to develop the population PK model. A total of 20,000 subjects were created and the exposure following the administration of a single dose of telavancin was simulated.

2.3 Objectives

The objectives of the population pharmacokinetic analysis included:

(a) Characterize the relationship between AUC of telavancin with BMI following a 10 mg/kg dose using a population PK model by simulating exposures in subjects with a range of BMI values; and (b) Quantify the magnitude of variability in the AUC of the obese population based on the variability observed in the population PK model in the adult telavancin population.

2.4 Analysis Assumptions

The assumptions underlying this analysis were as follows:

(a) A hierarchical (population) model can account for the two levels of variability inherent in repeated measurement designs—inter-individual and intra-individual variability;

(b) The pharmacokinetic parameters are log-normally distributed;

(c) The random effects describing inter-individual variability) in pharmacokinetic parameters are independent, normally distributed with mean zero and a variance $\omega^2$; and (d) The random effects describing intra-individual variability or residual error ($\varepsilon_{ij}$) are independent, normally distributed with mean zero and a variance $\sigma^2$.

2.5 Population Pharmacokinetic Model in Obese Subjects 2.5.1 Data

A population PK model for telavancin in adults was developed using the combined datasets from Phase 1, 2 and Phase 3 HAP and cSSSI studies where plasma concentrations of telavancin were assayed in patients (Tables 2-1A and 2-1B). Data was collated from 1,034 subjects, 641 males and 393 females (7,262 plasma samples) ranging in age from 18 to 100, with measured body weights between 33.6 to 314 kg, calculated BMI between 12.3 and 94 kg/m$^2$, and creatinine clearances (Cockcroft-Gault at screening using ideal body weight) between 3 and 150 mL/min.

TABLE 2-1A

Summary of Clinical Studies Used in the Population PK Analysis
Clinical Pharmacology

| Study ID (used as reference) | Acronym | Type of Study | Description | PLAC | TLV | COMP |
|---|---|---|---|---|---|---|
| 0027 | | Healthy subject PK | 14C-Telavancin (TLV) ADME | | 6 | |
| I6424-(101a) | | | Part 1, single dose (0.25-25 mg/kg); Part 2, 7 days 7.5-12.5-15 mg/kg | 17 + 7 | 25 + 20 | |
| I6424-(104a) | | | Thorough QTc; 7.5 and 15 mg/kg | 40 | 40 + 39 | 40 |
| I6424-(107a) | | | Skin blister fluid penetration | | 9 | |
| I6424-(108a) | | | Lung fluid penetration | | 20 | |
| I6424-(105a) | | Intrinsic factor PK | Healthy elderly Adults, 10 mg/kg | | 16 | |
| I6424-(102a) | | | Healthy elderly Adults, 12.5 mg/kg | 5 | 6 | |
| I6424-(103a) | | | Impaired renal function | | 29 | |
| 0016 | | | Impaired hepatic function | | 16 | |
| 0032 | | Extrinsic factor PK | Midazolam interaction | | 16 | |
| 0035 | | | Aztreonam 2 g and Piperacillin 4 g/tazobactam 0.5 g interaction | | 14 + 12 | |

TABLE 2-1A-continued

Summary of Clinical Studies Used in the Population PK Analysis
Clinical Pharmacology

| Study ID (used as reference) | Acronym | Type of Study | Description | PLAC | TLV | COMP |
|---|---|---|---|---|---|---|
| 1407 | | Renal PK | Renal function PK 10 mg/kg | | 45 | |
| 2403 | | Renal PK | Renal impairment PK 10 mg/kg | | 43 | |

PLAC: The number of subjects in the placebo arm.
TLV: The number of subjects in the telavancin treated arm.
COMP: The number of subjects in the comparator arm.

TABLE 2-1B

Summary of Clinical Studies Used in the Population PK Analysis
Efficacy and Safety Studies

| Study ID (used as reference) | Acronym | Type of Study | Description | PLAC | TLV |
|---|---|---|---|---|---|
| 16424-(202a) | FAST | Phase 2, Non-inferiority margin 20% | TLV 7.5 mg/kg, 4-10 days in SSTI vs. VANC or antistaphylococcal penicillin | 84 | 85 |
| 16424-(202b), before dose amendment | FAST-2 | | TLV 7.5 mg/kg in SSTI vs. VANC or antistaphylococcal penicillin | 15 | 17 |
| 16424-(202b), after dose amendment | FAST-2 | | TLV 10 mg/kg in SSTI vs. VANC or antistaphylococcal penicillin | 103 | 98 |
| 0017, before dose amendment | ATLAS-1 | Phase 3, Non-inferiority Margin 10% | TLV 7.5 mg/kg, 7-14 days in cSSTI vs. VANC | 73 | 70 |
| 0017, after dose amendment | | | TLV 10 mg/kg, 7-14 days in cSSTI vs. VANC | 429 | 433 |
| 0018, before dose amendment | ATLAS-2 | | TLV 7.5 mg/kg, 7-14 days in cSSTI vs. VANC | 20 | 19 |
| 0018, after dose amendment | | | TLV 10 mg/kg, 7-14 days in cSSTI vs. VANC | 517 | 518 |
| 16424-(203a) | | Phase 2 | *S. aureus* uncomplicated blood stream infection | 60 | |
| 0015 | ATTAIN | Phase 3, Non-inf. Margin 20% | TLV 10 mg/kg, 7-21 days in Hospital Acquired Pneumonia vs. VANC | 372 | 374 |
| 0019 | | | | 379 | 378 |

PLAC: The number of subjects in the placebo arm.
TLV: The number of subjects in the telavancin treated arm.

2.5.2 Generation of a Simulated Population of Normal and Obese Subjects

A simulated population was generated using the demographic data from the Phase 1, 2 and 3 studies in telavancin. 20,000 subjects were generated by sampling (with replacement) from the clinical trial dataset, with subjects evenly distributed across each of the five categories of obesity as classified by the WHO (Table 2-2).

4,000 subjects were generated for each of the five categories of obesity based on BMI by sampling from the demographic data. The BMI of the simulated subjects was restricted to be between 18.5 and 60 kg/m² to remove extreme outliers in the population. The height and weight corresponding to the sampled BMI was incorporated into the simulation dataset. The age of the subjects was based on the distribution of ages in the demographic data between 18 and 60. The baseline creatinine clearance of the subjects was based on the distribution of creatinine clearances in the demographic data between 80 and 150 mL/min. Gender was randomly assigned using a binomial distribution of males and females with equal probability for each gender. Simulated subjects were specified as uninfected. Table 2-3 describes the demographic characteristics of the simulated population.

All subjects were administered simulated doses of 10 mg/kg as adjustment for renal function was not required.

TABLE 2-2

Definition of WHO Obesity Categories

| WHO Obesity Classification | BMI kg/m² |
|---|---|
| Normal | 18.5-24.9 |
| Pre-Obese | 25.0-29.9 |
| Obese Class I | 30.0-34.9 |
| Obese Class II | 35.0-39.9 |
| Obese Class III | ≥40.0 |

2.5.3 Covariates in Adult Model

Covariates that describe the variability in the PK were identified in a previous population PK analysis of telavancin (see Example 1).

2.5.4 Population PK Model

| Pharmacokinetic parameter | Combined model |
|---|---|
| Cl, liters/h | $1.15 \cdot (CrCl/99)^{0.454} \cdot (AGE/46)^{0.173} \cdot (WT/77)^{0.352} \cdot GEND \cdot CSSSI1$ |
| $V_1$, liters | $6.11 \cdot (CrCl/99)^{-0.214} \cdot (AGE/46)^{0.229} \cdot (WT/77)^{0.847}$ |
| Q, liters/h | $4.72 \cdot (CrCl/99)^{0.211} \cdot CSSSI2$ |

-continued

| Pharmacokinetic parameter | Combined model |
|---|---|
| $V_2$, liters | $6.46 \cdot (CrCl/99)^{0.127} \cdot (AGE/46)^{0.381} \cdot (WT/77)^{0.548} \cdot CSSSI3$ |

GEND = 1 for males, 0.933 for females
CSSSI1 = 1 for uninfected or HAP, 0.946 for cSSSI subject
CSSSI2 = 1 for uninfected or HAP, 1.62 for cSSSI subject
CSSSI3 = 1 for uninfected, 1.14 for cSSSI subject

| Model | OFV | Population estimate ± SE | Between subject variability (%) |
|---|---|---|---|
| Final Model | 34523.584 | | |
| Cl (L/hr) | | 1.15 ± 0.04 | 29.8 |
| V1 (L) | | 6.11 ± 0.23 | 42.1 |
| Q (L/hr) | | 4.72 ± 0.34 | 38.1 |
| V2 (L) | | 6.46 ± 0.22 | 29.5 |
| Residual variability | | | |
| Proportional error | | 17% | |
| Additive error | | 0.36 µg/mL | |

2.5.5 Simulation of Telavancin Exposures

Telavancin PK profiles were simulated for each obese subject using the estimated PK parameters and inter-individual errors determined during the population PK analysis based on the administered dose as recorded in the dataset. The individually estimated PK parameters for each subject were determined based upon the specific intra and inter-individual errors determined using nonlinear mixed effect analysis.

Individually predicted (IPRED) plasma concentrations at 0, 0.5, 1, 1.5, 2, 3, 4, 5, 6, 8, 12, 18, and 24 hours after the infusion of a single-dose of telavancin were simulated for each subject, with exposure over 24 hours calculated using the linear trapezoidal method. $C_{max}$ was the maximum plasma concentration of telavancin over the 24 hour dosing period.

2.6 Results

2.6.1 Validation of Population PK Model in Obese Subjects

Standard plots (observed vs. predicted values, weighted residuals) were used to visually evaluate the goodness of fit of the population PK model in each category for obesity. The number of plasma concentration measurements and the number of subjects between the ages of 18 and 60 with a creatinine clearance >80 mL/min used to evaluate the goodness of fit is summarized in Table 2-2.

In all five categories, the observed vs. predicted plasma concentrations of telavancin were comparable to the line of identity (FIG. 6A-E). In all five categories, the weighted residuals were evenly distributed around 0 with the majority of residuals between −2 and 2 (FIG. 7A-E).

2.6.2 Demographics of Simulated Obese Subjects

A total of 20,000 PK profiles were simulated in this analysis. The simulated individual subject profiles were evenly distributed across the five categories of obesity with a mean age of 40 and a mean CrCl of 114 mL/min (Table 2-3).

TABLE 2-3

Demographics of Simulated Population of Subjects

| n | Normal 4000 | Pre-Obese 4000 | Obese Class I 4000 | Obese Class II 4000 | Obese Class III 4000 |
|---|---|---|---|---|---|
| AGE (years) | 40 ± 12 | 39 ± 12 | 39 ± 12 | 39 ± 12 | 39 ± 12 |
| WEIGHT (kg) | 67 ± 10 | 80 ± 10 | 92 ± 12 | 107 ± 14 | 130 ± 21 |
| BMI (kg/m²) | 22.6 ± 1.6 | 27.2 ± 1.4 | 32.2 ± 1.4 | 36.9 ± 1.4 | 45.5 ± 5.3 |
| CrCl (mL/min) | 112 ± 19 | 111 ± 17 | 111 ± 17 | 111 ± 18 | 112 ± 17 |
| Gender | 1958M, 2042F | 1986M, 2014F | 2011M, 1989F | 2015M, 1985F | 2017M, 1983F |

2.6.3 Drug Exposure in Obese Subjects

Figure 8A:
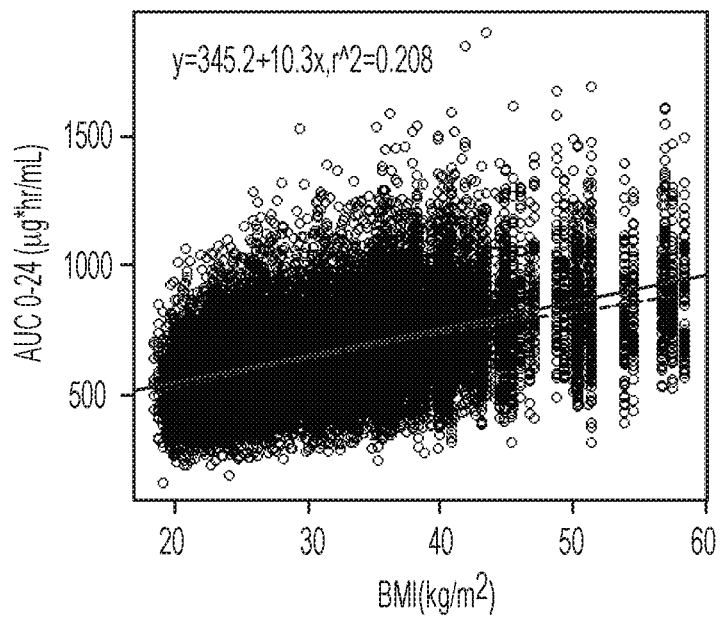
FIG. 8A is a scatter plot of the predicted telavancin $AUC_{0-24h}$ versus BMI.
Figure 8B:
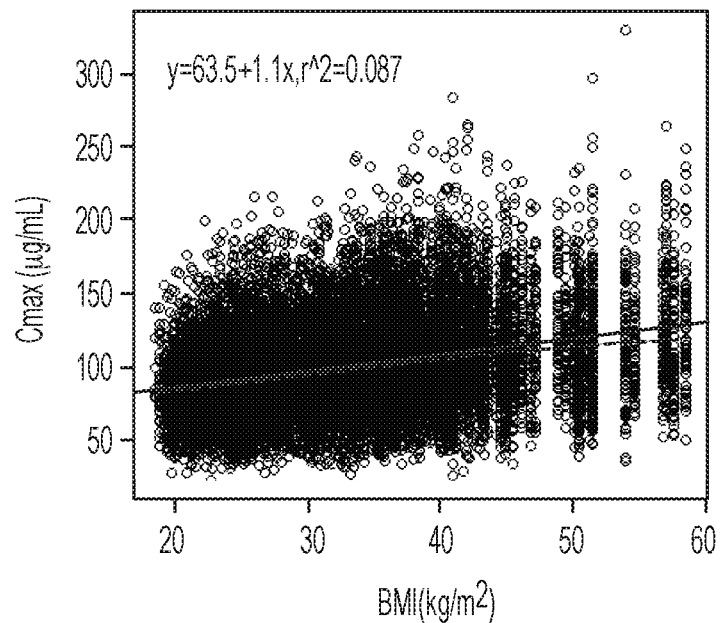
FIG. 8B is a scatter plot of the predicted telavancin $C_{max}$ versus BMI.
Figure 9:
FIG. 9 shows predicted telavancin total exposure ($AUC_{0-24h}$) by obesity category.
Figure 10:
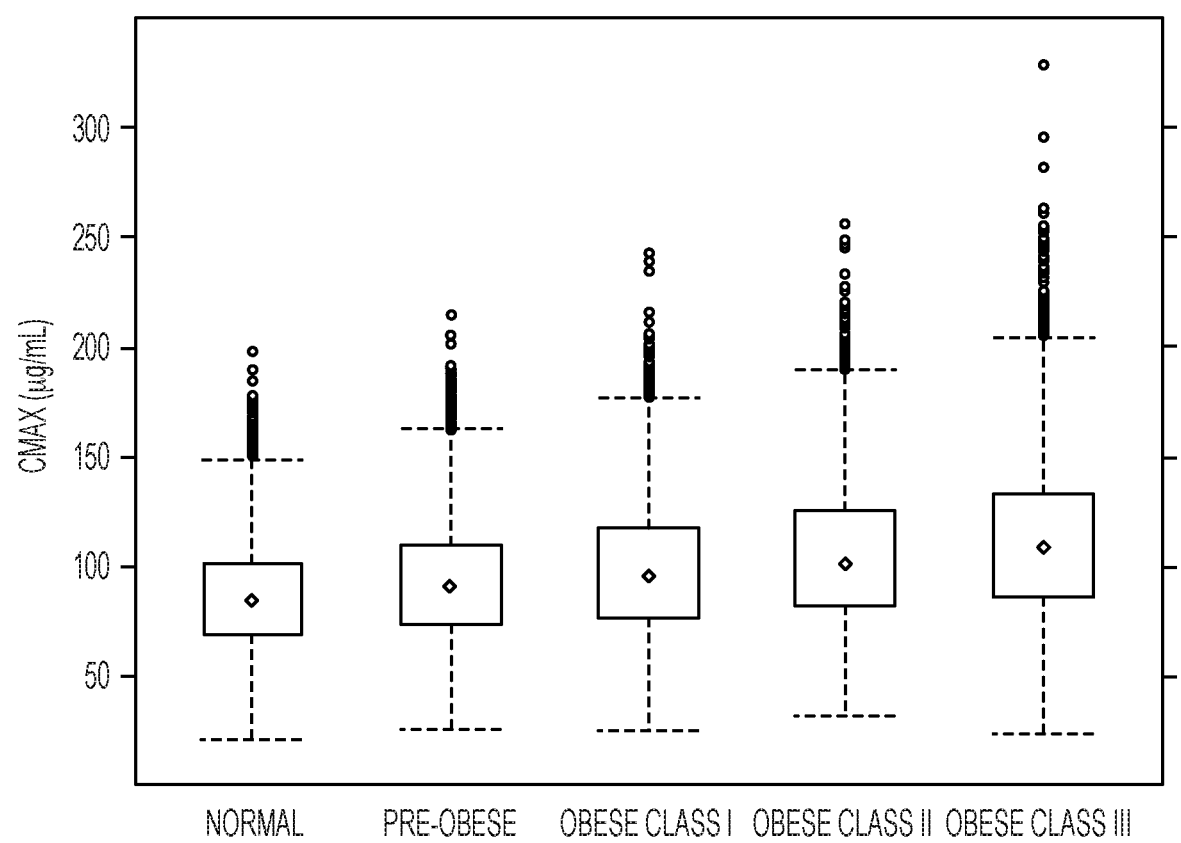
FIG. 10 shows predicted telavancin maximum exposure ($C_{max}$) by obesity category.

Exposure to telavancin increased in subjects with increasing BMI (Table 2-5). FIG. 9 and FIG. 10 show the range of exposures for simulated subjects in each obesity category. A simple linear regression model with $AUC_{0-24h}$ as the dependent variable and BMI as the independent variable estimated that $AUC_{0-24h}$ increases 10.3 µg·hr/mL for every increase of 1 kg/m² in BMI while $C_{max}$ increases 1.1 µg/mL for every increase of 1 kg/m² in BMI (FIG. 8A and FIG. 8B).

TABLE 2-4

Summary of Linear Regression on Exposure
($AUC_{0-24\ h}$ and $C_{max}$) as a Function of BMI

```
Call:
lm(formula = df.AUC$AUC~df.AUC$BMI)
Residuals:
   Min     1Q Median     3Q    Max
-555.89 -117.97 -16.64 100.83 1118.81
Coeffiecients:
              Estimate Std. Error t value Pr(>|t|)
(Intercept)   345.1641   4.8380   71.34   <2e-16 ***
df.AUC$BMI     10.3432   0.1426   72.55   <2e-16 ***
---
Signif. codes:  0 '***' 0.001 '**' 0.01 '*' 0.05 '.' 0.1 ' ' 1
Residual standard error: 169.1 on 19998 degrees of freedom
Multiple R-squared: 0.2084, Adjusted R-squared: 0.2083
F-statistic: 5263 on 1 and 19998 DF, p-value: <2.2e-16
Call:
lm(formula = df.AUC$CMAX~df.AUC$BMI)
Residuals:
   Min     1Q Median     3Q    Max
-88.069 -21.147 -3.041 17.833 205.064
Coefficients:
              Estimate Std. Error t value Pr(>|t|)
(Intercept)   63.5406   0.8585   74.01   <2e-16 ***
df.AUC$BMI     1.1015   0.0253   43.54   <2e-16 ***
---
Signif. codes:  0 '***' 0.001 '**' 0.01 '*' 0.05 '.' 0.1 ' ' 1
Residual standard error: 30 on 19998 degrees of freedom
Multiple R-squared: 0.08658, Adjusted R-squared: 0.08653
F-statistic: 1896 on 1 and 19998 DF, p-value: <2.2e-16
```

The percentage increases in AUC relative to the subjects of normal weight were 11, 19, 30 and 43% for the pre-obese and obese class I, II and III respectively. The percentage increases in $C_{max}$ relative to the subjects of normal weight were 8, 14, 21 and 29% for the pre-obese and obese class I, II and III respectively.

TABLE 2-5

Telavancin Exposure in Simulated Population of Subjects

|  | Normal | Pre-Obese | Obese Class I | Obese Class II | Obese Class III |
|---|---|---|---|---|---|
| $AUC_{0-24\,h}$ (µg · hr/mL) | 569 ± 143 | 632 ± 156 | 677 ± 165 | 737 ± 183 | 811 ± 200 |
| $C_{max}$(µg/mL) | 87 ± 25 | 94 ± 27 | 99 ± 30 | 105 ± 32 | 113 ± 36 |

2.7 Discussion

The objective of this analysis was to simulate the exposure of telavancin following a single 10 mg/kg dose administration in an obese population. Based upon the simulated exposures across a range of BMI, the exposure of obese subjects to telavancin is expected to increase with BMI. The trend in increased exposures with increased BMI was approximately linear with a 9% increase in $AUC_{0-24h}$ and a 6% increase in $C_{max}$ with each obesity category (FIG. 9 and FIG. 10).

2.8 Conclusions

At a dose of 10 mg/kg, the exposure is anticipated to result in increased plasma exposure to telavancin in the obese population with normal renal function by 43% ($AUC_{0-24h}$) and 29% ($C_{max}$) in the subjects with BMI >40 kg/m². The increase was predicted to be linear over the range of BMI and is reflective of the weight-based dosing regimen for telavancin.

Example 3

Logistic Regression Analysis of Individually Predicted Telavancin Pharmacokinetic Exposure and Outcomes in HABP/VABP and cSSSI Phase 3 Studies 3.1 Summary The objective of this post-hoc analysis was to quantify exposure-response relationships between the plasma exposure to telavancin and the following outcomes: 28-day all-cause mortality, acute kidney injury (AKI) and clinical response at test of cure (TOC) in all Phase 3 hospital acquired bacterial pneumonia/ventilator acquired bacterial pneumonia (HABP/VABP) and complicated skin and skin structural infection (cSSSI) patients (Studies 0015, 0019, 0017 and 0018) treated with telavancin. Binomial logistic regression analysis was used to determine the probability of each of the aforementioned outcome measures as a function of estimated telavancin exposures from a population PK model (in subjects where plasma concentrations were measured).

Exposure ($AUC_{0-24h}$) to telavancin for subjects where plasma concentrations were measured was estimated using a population PK model developed using all clinical data. Individually predicted steady state exposures were based on measured plasma concentrations collected 4 to 6 days after the first dose of telavancin.

In HABP/VABP subjects with renal impairment (CrCl≤50 mL/min), telavancin exposure had a significant impact on the probability of 28-day all-cause mortality. Increased exposure was associated with an increased probability of death in this patient subpopulation. However, there was no significant impact on the probability of 28-day all-cause mortality for all HABP/VABP subjects.

In all Phase 3 subjects and cSSSI subjects, telavancin exposure had a significant impact on the probability of AKI, i.e., increased exposure was associated with an increased probability of AKI. However, in HABP/VABP subjects alone there was no significant impact on the probability of AKI.

In all Phase 3 subjects, telavancin exposure did not have a significant impact on the probability of clinical response at TOC.

3.2. Introduction

This analysis was designed to describe the relationship between exposure and response in patients treated with telavancin. Individually predicted exposures of telavancin in Phase 3 subjects where plasma telavancin was measured (n=579) were estimated using a population PK model of telavancin developed from Phase 1, 2 and 3 clinical studies. The telavancin exposure was predicted using the individually estimated clearance, volume of distribution, intercompartmental clearance and volume of the secondary compartment for each subject with no residual error.

This analysis uses a consistent method to predict exposure to telavancin in both HABP/VABP and cSSSI subjects. Exposure to telavancin was previously calculated utilizing the linear trapezoidal method based on four sparse samples from each subject, collected during the first 12 (HABP/VABP) or 4 hours (cSSSI).

Logistic regression analysis was used to parameterize the relationship between exposure ($AUC_{0-24h}$) and the probability of 28-day all-cause mortality, AKI (defined as a 50% increase or greater than 0.5 mg/dL increase in serum creatinine) and clinical response at test of cure (TOC) for all Phase 3 subjects. The analysis was repeated for the individual HABP/VABP and cSSSI subpopulations.

3.3 Objectives

The objectives of this analysis were:

(a) Identify and characterize the exposure-response relationship between telavancin exposure and the following outcomes in Phase 3 trials in cSSSI and HABP/VABP:

(i) 28-day all-cause mortality (HABP/VABP only);

(ii) Acute kidney injury (AKI); and (iii) Clinical response at test of cure (TOC).

3.4 Logistic Regression Analysis in Phase 3 Subjects with PK Data 3.4.1 Data The data for the analysis was based upon 579 subjects from Studies 0015, 0017, 0018 and 0019. The population consisted of 196 HABP/VABP subjects and 383 cSSSI subjects, 341 males and 238 females, ranging in age from 18 to 100 years with measured body weights from 34 to 314 kg, calculated BMI between 12 and 94 kg/m², and creatinine clearances (Cockcroft-Gault at screening) between 5 and 367 mL/min (Table 3-1). Of the 373 subjects in the studies with cSSSI where PK samples were taken, only 1 subject died during the clinical trial.

TABLE 3-1

Demographics of Analysis Population

Mean ± SD (range)

| | HABP/VABP | cSSSI | Total |
|---|---|---|---|
| n | 196 | 383 | 579 |
| AGE (years) | 63 ± 18 (20, 100) | 44 ± 15 (18, 89) | 51 ± 18 (18, 100) |
| WEIGHT (kg) | 76 ± 22 (34, 171) | 83 ± 27 (39, 314) | 81 ± 26 (34, 314) |
| HEIGHT (cm) | 169 ± 11 (122, 195) | 171 ± 10 (140, 200) | 170 ± 11 (122, 200) |
| BMI (kg/m$^2$) | 26 ± 7 (12, 65) | 29 ± 9 (13, 94) | 27.8 ± 8.3 (12, 94) |
| CrCl (mL/min) | 85 ± 51 (5, 368) | 106 ± 35 (18, 249) | 99 ± 43 (5, 367) |
| SEX | F = 73, M = 123 | F = 165, M = 218 | F = 238, M = 341 |
| AUC$_{0-24}$ (µg · hr/mL) | 670 ± 231 (273, 1370) | 671 ± 206 (247, 1512) | 671 ± 214 (247, 1512) |
| MORTALITY | Y = 45, N = 151 | Y = 1, N = 382 | Y = 46, N = 533 |
| AKI | Y = 39, N = 157 | Y = 39, N = 343, UNKNOWN = 1 | Y = 78, N = 500, UNKNOWN = 1 |
| CURE | CURE = 127, INDETERMINATE = 16, NOT CURED = 0, FAILURE = 28, UNKNOWN = 25 | CURE = 322, INDETERMINATE = 8, NOT CURED = 30, FAILURE = 0, UNKNOWN = 23 | CURE = 449, INDETERMINATE = 24, NOT CURED = 30, FAILURE = 28, UNKNOWN = 48 |

The population PK model for telavancin in adults was developed using the combined datasets from Phase 1, 2 and Phase 3 HABP/VABP and cSSSI studies where plasma concentrations of telavancin were assayed in patients (see Table 2-1A and 2-1B above). Data was collated from 1,034 subjects, 641 males and 393 females (7262 plasma samples) ranging in age from 18 to 100, with measured body weights between 33.6 to 314 kg, calculated BMI between 12.3 and 94 kg/m$^2$, and creatinine clearances (Cockcroft-Gault at screening using ideal body weight) between 3 and 150 mL/min.

3.4.2 Software and Platform

Data manipulation and logistic regression analyses were carried out using R version 3.0.2 (The R project for Statistical Computing, http://www.r-project.org). PK estimated concentrations were generated using NONMEM version 7.2 (ICON plc, Dublin, Ireland) on a Windows 7 platform with gfortran (the GNU Fortran compiler version 4.6.0).

3.4.3 Prediction of Telavancin Exposures in Phase 3 All-Treated Subjects

Telavancin PK profiles were predicted for each Phase 3 subject where PK samples were collected (n=579).

The predicted telavancin PK profiles for each subject were generated using the individually estimated PK parameters determined during the population PK analysis based on the administered dose as recorded in the dataset. The individually estimated PK parameters for each subject were determined based upon the specific intra- and inter-individual errors determined using nonlinear mixed effect analysis.

Steady state plasma concentrations at 0, 0.5, 1, 1.5, 2, 3, 4, 5, 6, 8, 12, 18, 24, 36 and 48 hours after the infusion of telavancin were calculated for each subject, with exposure over 24 hours (AUC$_{0-24h}$) calculated using the linear trapezoidal method.

3.4.4 Logistic Regression Analysis Approach

Logistic regression analyses were conducted on the Phase 3 dataset using individually predicted exposure (AUC$_{0-24h}$) and the outcomes of interest (28-day all-cause mortality, AKI, and clinical response at TOC). The analysis was performed using the generalized linear model function in R specifying a binomial variance and the logit link function.

The output produced for each logistic regression analysis includes indices of fit (i.e., null and deviance residuals, Akaike's information criterion and likelihood ratio test statistics to provide an assessment of model improvement as additional parameters are included in the model).

3.5 Results 3.5.1 Validation of Population PK Model in Phase 3 Subjects

Figure 11A:
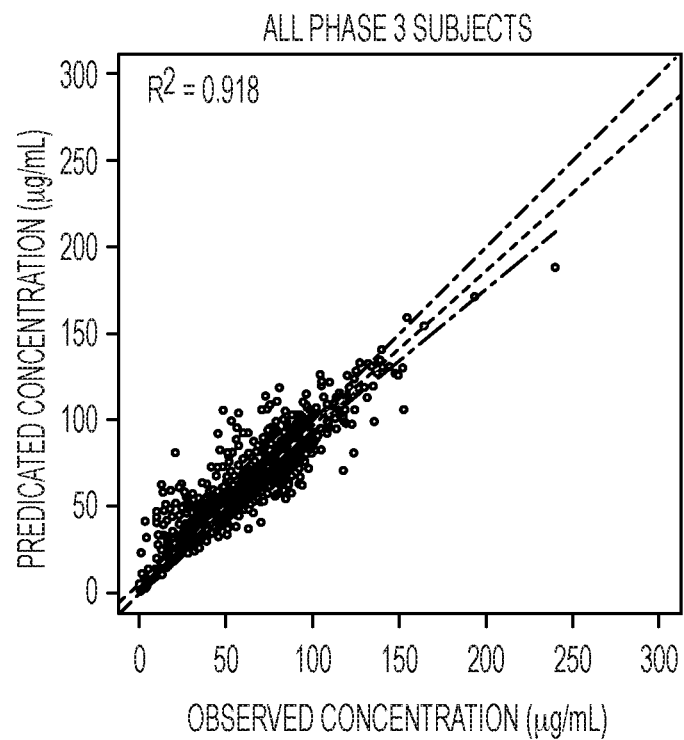
FIG. 11A shows a plot of individually predicted exposure versus observed concentration (μg/mL) for all Phase 3 subjects where PK samples were collected (n=579).
Figure 11B:
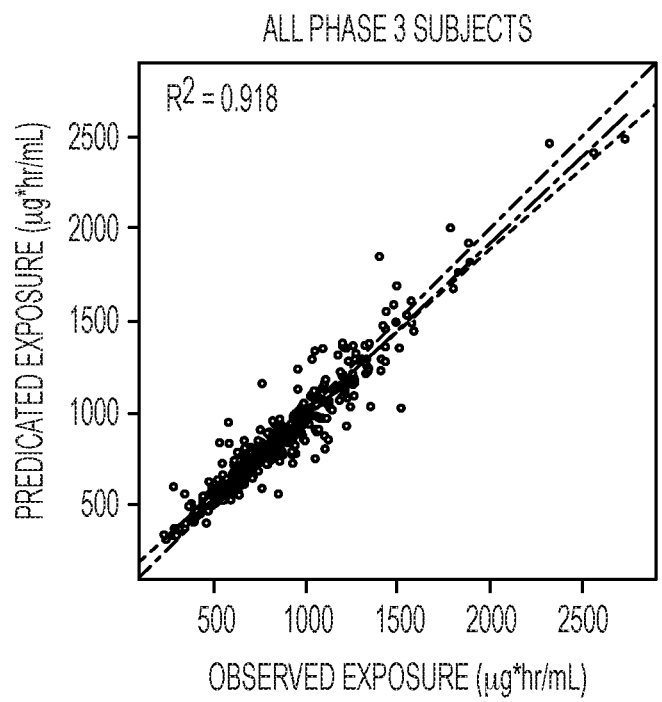
FIG. 11B shows a plot of for individually predicted exposure versus observed exposure ($AUC_{0-24h}$) for all Phase 3 subjects where PK samples were collected (n=579).

Standard plots (observed vs. predicted values) were used to visually evaluate the goodness-of-fit of the individually predicted exposures as determined using the population PK model compared to the observed exposures based on the four measured plasma concentrations (FIG. 11B). The linear regression fit of observed versus predicted Phase 3 exposures had an R$^2$ of 0.918.

Figure 12A:
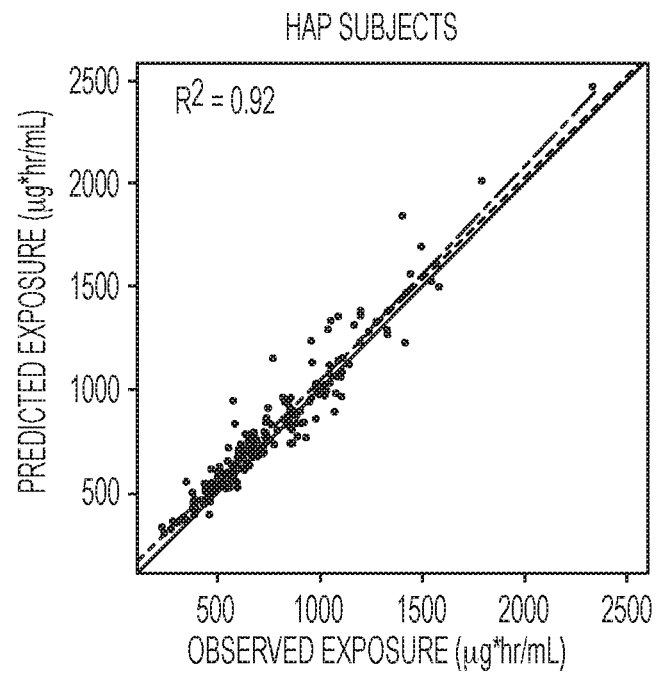
FIG. 12A shows a plot of individually predicted exposure versus measured exposure ($AUC_{0-24h}$) for all HABP/VABP subjects where PK samples were collected.
Figure 12B:
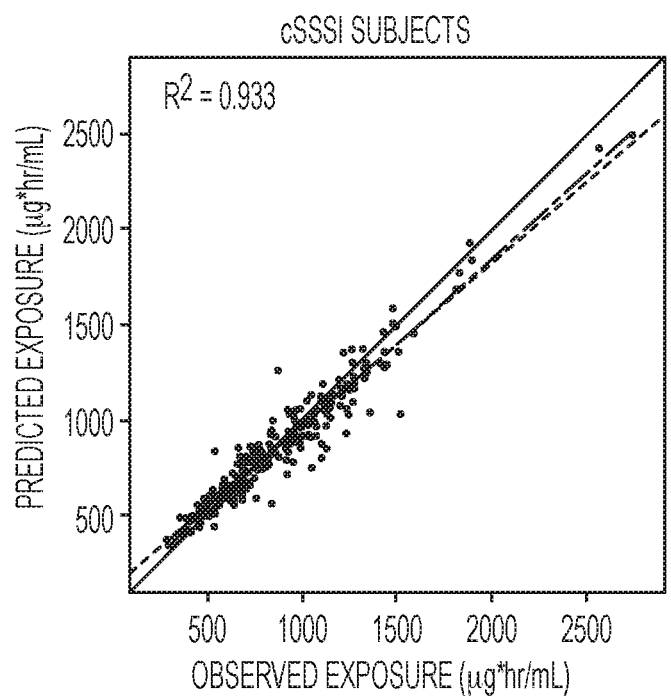
FIG. 12B shows a plot of individually predicted exposure versus measured exposure ($AUC_{0-24h}$) for all cSSSI subjects where PK samples were collected.

An R$^2$ value of 0.92 and 0.933 resulted from the linear regression fit of the observed versus predicted values of the HABP/VABP and cSSSI populations respectively (FIG. 12A and FIG. 12B).

3.5.2 Exposure-Response Relationship in the Phase 3 Population

Figure 13A:
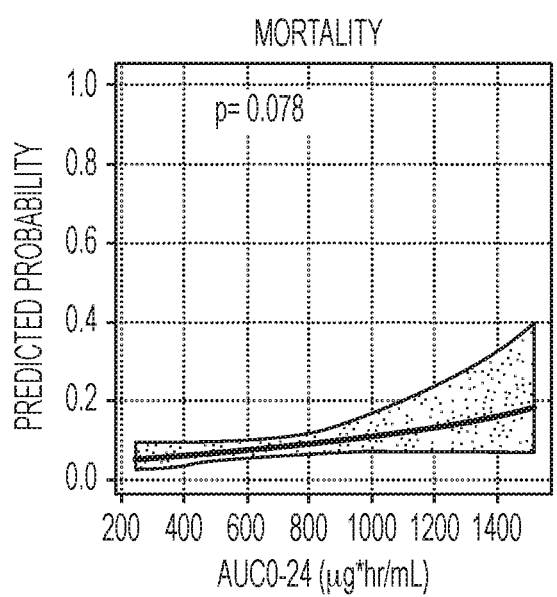
FIG. 13A shows logistic regression fit for 28-day all-cause mortality as a function of exposure ($AUC_{0-24h}$) for all Phase 3 subjects where PK samples were collected (n=579).
Figure 13B:
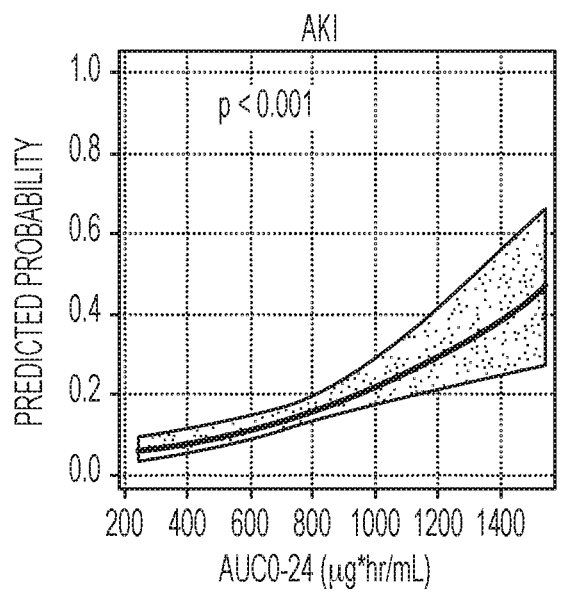
FIG. 13B shows logistic regression fit for AKI as a function of exposure ($AUC_{0-24h}$) for all Phase 3 subjects where PK samples were collected (n=579).
Figure 13C:
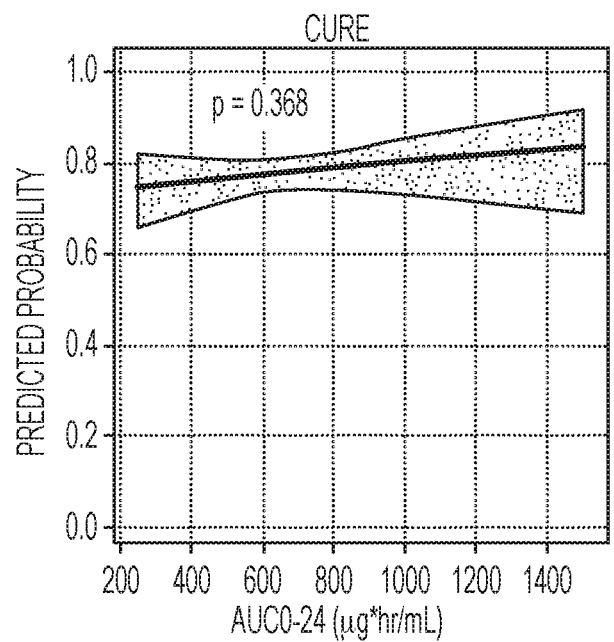
FIG. 13C shows logistic regression fit for clinical response at TOC as a function of exposure ($AUC_{0-24h}$) for all Phase 3 subjects where PK samples were collected (n=579).

Logistic regression models were fit to determine whether predicted exposures from the population PK model could adequately predict the probability of 28-day all-cause mortality (Table 3-3), AKI (Table 3-4) and clinical response at TOC (Table 3-5) (FIG. 13A-C).

Exposure (AUC$_{0-24h}$) did not have a significant impact on the probability of 28-day all-cause mortality (p=0.078) (FIG. 13A).

TABLE 3-3

Summary of Logistic Regression of 28-day All-Cause Mortality as a Function of Steady State Exposure (AUC$_{0-24\ h}$) in all (HABP/VABP and cSSSI) Phase 3 Subjects

| Coefficient | Estimate | Std. Error | Pr(>|z|) | Odds Ratio |
|---|---|---|---|---|
| Intercept | −3.26 | 0.50 | 7.46e−11* | 0.038 |
| Steady State AUC$_{0-24\ h}$ | 1.16e−3 | 6.63e−4 | 0.078 | 1.001 |
| Pearson Chi-squared Goodness of Fit | | | 1.00 | |
| Hosmer-Lemeshow Goodness of Fit | | | 0.127 | |

*p < 0.05

Exposure (AUC$_{0-24h}$) had a significant impact on the probability of AKI (p<0.001), i.e., with an increase in exposure, there is an increase in the probability of AKI (Table 3-4) (FIG. 13B).

TABLE 3-4

Summary of Logistic Regression of AKI as a Function of Steady State Exposure ($AUC_{0-24\ h}$) in all Phase 3 Subjects

| Coefficient | Estimate | Std. Error | Pr(>|z|) | Odds Ratio |
|---|---|---|---|---|
| Intercept | −3.36 | 0.41 | 2.90e−16* | 0.034 |
| Steady State $AUC_{0-24\ h}$ | 2.12e−3 | 5.28e−4 | 5.79e−05* | 1.002 |
| Pearson Chi-squared Goodness of Fit | | | 1.00 | |
| Hosmer-Lemeshow Goodness of Fit | | | 0.658 | |

*p < 0.05

Exposure ($AUC_{0-24h}$) did not have a significant impact on the probability of clinical response at TOC (p=0.368) (Table 3-5) (FIG. 13C).

TABLE 3-5

Summary of Logistic Regression of Clinical Response at TOC as a Function of Steady State Exposure ($AUC_{0-24\ h}$) in all Phase 3 Subjects

| Coefficient | Estimate | Std. Error | Pr(>|z|) | Odds Ratio |
|---|---|---|---|---|
| Intercept | 0.95 | 0.33 | 3.83e−3* | 2.596 |
| Steady State $AUC_{0-24\ h}$ | 4.29e−3 | 4.77e−4 | 0.368 | 1.000 |
| Pearson Chi-squared Goodness of Fit | | | 0.127 | |
| Hosmer-Lemeshow Goodness of Fit | | | 0.213 | |

*p < 0.05

3.5.3 Exposure-Response Relationship in the All-Treated HABP/VABP Population Logistic regression models were fit to determine whether predicted exposures from the population PK model could adequately predict the probability of 28-day all-cause mortality (Table 3-6), AKI (Table 3-7) and clinical response at TOC (Table 3-8) in HABP/VABP subjects.

Figure 14A:
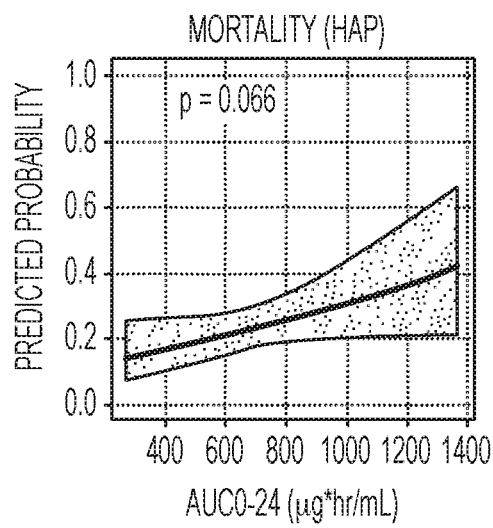
FIG. 14A shows logistic regression fit for 28-day all-cause mortality as a function of exposure ($AUC_{0-24h}$) for all Phase 3 HABP/VABP subjects where PK samples were collected (n=196).

Exposure ($AUC_{0-24h}$) did not have a significant impact on the probability of 28-day all-cause mortality (p=0.066) in HABP/VABP subjects (FIG. 14A).

TABLE 3-6

Summary of Logistic Regression of 28-day All-Cause Mortality as a Function of Steady State Exposure ($AUC_{0-24\ h}$) in all HABP/VABP Subjects

| Coefficient | Estimate | Std. Error | Pr(>|z|) | Odds Ratio |
|---|---|---|---|---|
| Intercept | −2.12 | 0.53 | 7.95e−5** | 0.119 |
| Steady State $AUC_{0-24\ h}$ | 1.33e−3 | 7.23e−4 | 0.066 | 1.001 |
| Pearson Chi-squared Goodness of Fit | | | 0.236 | |
| Hosmer-Lemeshow Goodness of Fit | | | 0.022* | |

*p < 0.05

Figure 14B:
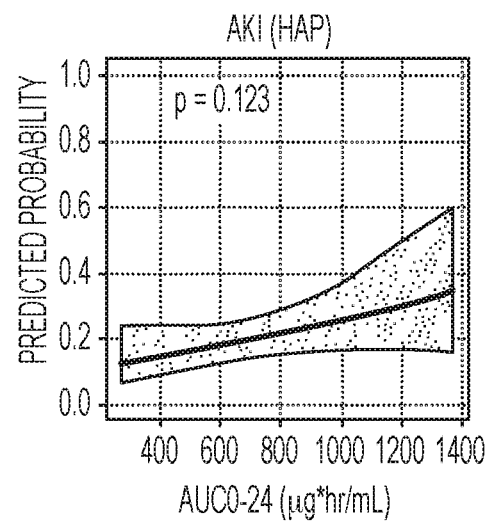
FIG. 14B shows logistic regression fit for AKI as a function of exposure ($AUC_{0-24h}$) for all Phase 3 HABP/VABP subjects where PK samples were collected (n=196).

Exposure ($AUC_{0-24h}$) did not have a significant impact on the probability of AKI (p=0.123) in HABP/VABP subjects (Table 3-7) (FIG. 14B).

TABLE 3-7

Summary of Logistic Regression of AKI as a Function of Steady State Exposure ($AUC_{0-24\ h}$) in all HABP/VABP Subjects

| Coefficient | Estimate | Std. Error | Pr(>|z|) | Odds Ratio |
|---|---|---|---|---|
| Intercept | −2.19 | 0.56 | 9.86e−5** | 0.111 |
| Steady State $AUC_{0-24\ h}$ | 1.16e−3 | 7.56e−4 | 0.123 | 1.001 |
| Pearson Chi-squared Goodness of Fit | | | 0.502 | |
| Hosmer-Lemeshow Goodness of Fit | | | 0.151 | |

*p < 0.05

Figure 14C:
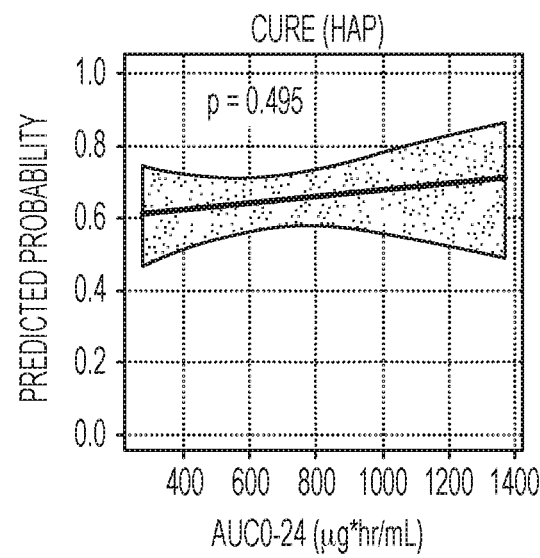
FIG. 14C shows logistic regression fit for clinical response at TOC as a function of exposure ($AUC_{0-24h}$) for all Phase 3 HABP/VABP subjects where PK samples were collected (n=196).

Exposure ($AUC_{0-24h}$) did not have a significant impact on the probability of clinical response at TOC (p=0.495) in HABP/VABP subjects (Table 3-8) (FIG. 14C).

TABLE 3-8

Summary of Logistic Regression of Clinical Response at TOC as a Function of Steady State Exposure ($AUC_{0-24\ h}$) in all HABP/VABP Subjects

| Coefficient | Estimate | Std. Error | Pr(>|z|) | Odds Ratio |
|---|---|---|---|---|
| Intercept | 0.31 | 0.46 | 0.502 | 1.364 |
| Steady State $AUC_{0-24\ h}$ | 4.50e−4 | 6.60e−4 | 0.495 | 1.000 |
| Pearson Chi-squared Goodness of Fit | | | 0.003* | |
| Hosmer-Lemeshow Goodness of Fit | | | 0.042* | |

*p < 0.05

Figure 15A:
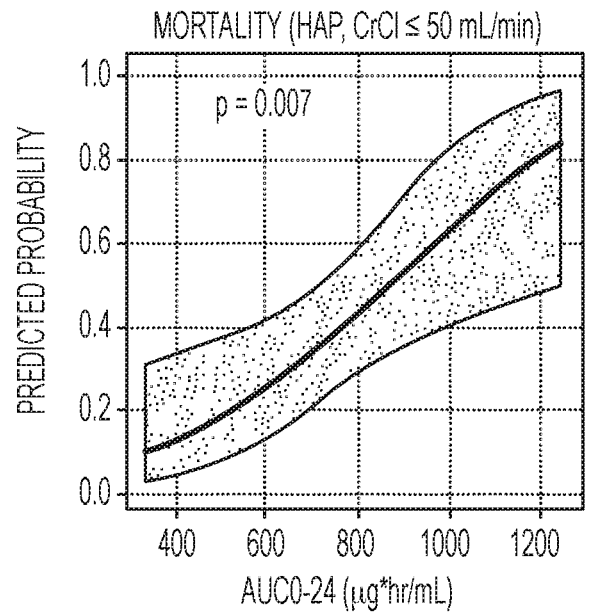
FIG. 15A shows logistic regression fit for 28-day all-cause mortality as a function of exposure ($AUC_{0-24h}$) for HABP/VABP subjects with renal impairment (CrCl≤50 mL/min) where PK samples were collected.
Figure 15B:
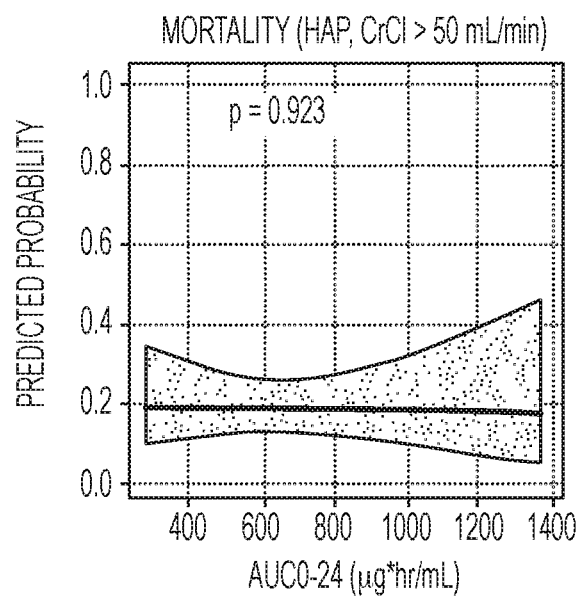
FIG. 15B shows logistic regression fit for 28-day all-cause mortality as a function of exposure ($AUC_{0-24h}$) for HABP/VABP subjects without renal impairment (CrCl>50 mL/min) where PK samples were collected.

In the subpopulation of HABP/VABP subjects with renal impairment (CrCl≤50 mL/min), exposure ($AUC_{0-24h}$) had a significant impact on the probability of 28-day all-cause mortality (p=0.007) (Table 3-9) (FIG. 15A).

TABLE 3-9

Summary of Logistic Regression of 28-day All-Cause Mortality as a Function of Steady State Exposure ($AUC_{0-24\ h}$) in HABP/VABP Subjects with Renal Impairment (CrCl ≤50 mL/min)

| Coefficient | Estimate | Std. Error | Pr(>|z|) | Odds Ratio |
|---|---|---|---|---|
| Intercept | −3.65 | 1.22 | 0.003* | 0.026 |
| Steady State $AUC_{0-24\ h}$ | 4.23e−3 | 1.58e−3 | 7.22e−3* | 1.004 |
| Pearson Chi-squared Goodness of Fit | | | 0.171 | |
| Hosmer-Lemeshow Goodness of Fit | | | 0.160 | |

*p < 0.05

3.5.4 Exposure Response Relationship in the All-Treated cSSSI Population

Figure 16A:
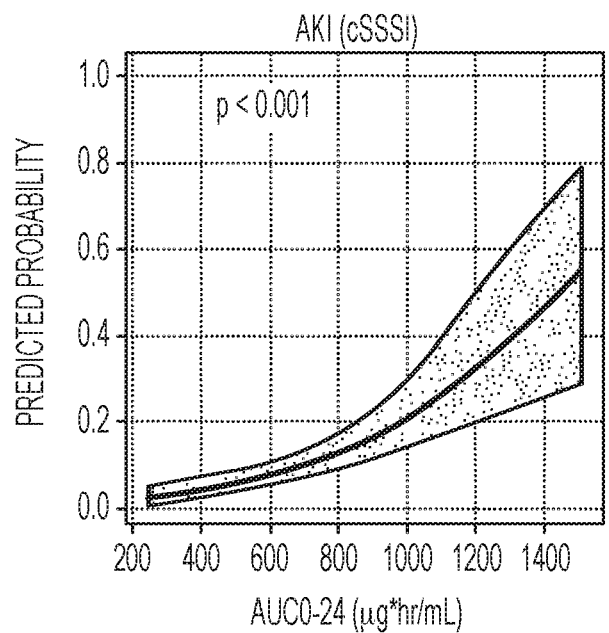
FIG. 16A shows logistic regression fit for AKI as a function of exposure ($AUC_{0-24h}$) for all Phase 3 cSSSI subjects where PK samples were collected (n=383).
Figure 17A:
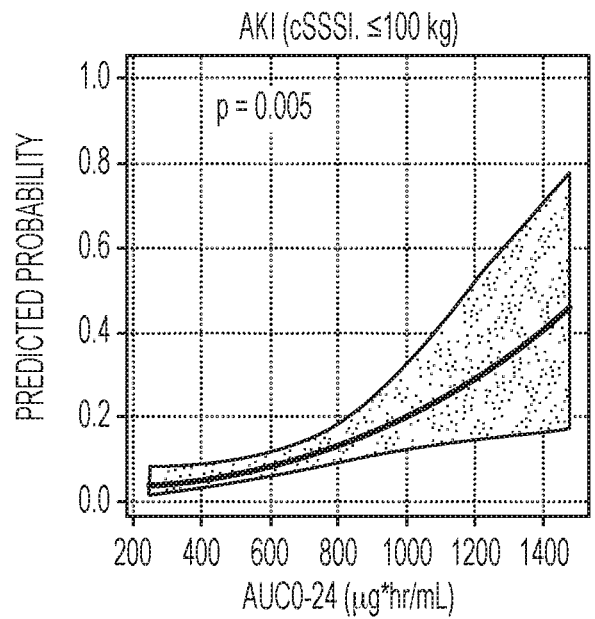
FIG. 17A shows logistic regression fit for AKI as a function of exposure ($AUC_{0-24h}$) for all Phase 3 cSSSI subjects below 100 kg where PK samples were collected.
Figure 17B:
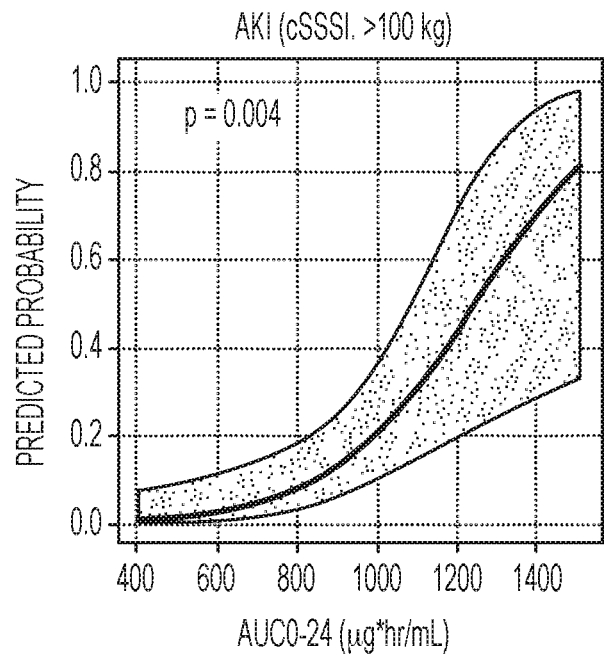
FIG. 17B shows logistic regression fit for AKI as a function of exposure ($AUC_{0-24h}$) for all Phase 3 cSSSI subjects above 100 kg where PK samples were collected.

Logistic regression models were fit to determine whether predicted exposures from the population PK model could adequately predict the probability of AKI (Table 3-10) and clinical response at TOC (Table 3-11) in cSSSI subjects. Logistic regression analysis was not performed for the dependent variable 28-day all-cause mortality in cSSSI subjects due to few cSSSI subjects that died during the study. Exposure ($AUC_{0-24h}$) had a significant impact on the probability of AKI (p<0.001) in cSSSI subjects. Increases in exposure ($AUC_{0-24h}$) were associated with an increase in the probability of AKI (FIG. 16A). In the subpopulation of cSSSI subjects with weight >100 kg, exposure ($AUC_{0-24h}$) had a greater magnitude of impact on the probability of AKI than for subjects with weight ≤100 kg (FIG. 17A and FIG. 17B).

TABLE 3-10

Summary of Logistic Regression of AKI as a Function of Steady State Exposure ($AUC_{0-24\ h}$) in all cSSSI Subjects

| Coefficient | Estimate | Std. Error | Pr(>\|z\|) | Odds Ratio |
|---|---|---|---|---|
| Intercept | −4.35 | 0.59 | 2.28e−13* | 0.013 |
| Steady State $AUC_{0-24\ h}$ | 3.01e−3 | 7.3e−4 | 4.11e−5* | 1.003 |
| Pearson Chi-squared Goodness of Fit | | | 1 | |
| Hosmer-Lemeshow Goodness of Fit | | | 0.209 | |

*p < 0.05

Figure 16B:
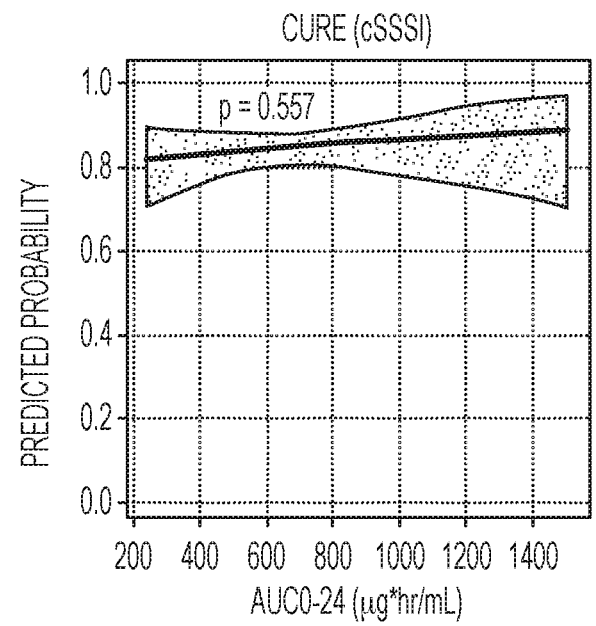
FIG. 16B shows logistic regression fit for clinical response at TOC as a function of exposure ($AUC_{0-24h}$) for all Phase 3 cSSSI subjects where PK samples were collected (n=383).

In cSSSI subjects, exposure ($AUC_{0-24h}$) does not have a significant impact on the probability of clinical response at TOC (p=0.557) (Table 3-11) (FIG. 16B).

TABLE 3-11

Summary of Logistic Regression of Clinical Response at TOC as a Function of Steady State Exposure ($AUC_{0-24\ h}$) in all cSSSI Subjects

| Coefficient | Estimate | Std. Error | Pr(>\|z\|) | Odds Ratio |
|---|---|---|---|---|
| Intercept | 1.39 | 0.48 | 3.96e−3* | 4.016 |
| Steady State $AUC_{0-24\ h}$ | 4.11e−4 | 7.0e−4 | 0.557 | 1.000 |
| Pearson Chi-squared Goodness of Fit | | | 0.955 | |
| Hosmer-Lemeshow Goodness of Fit | | | 0.850 | |

*p < 0.05

3.6 Discussion

Logistic regression analysis methods were used to determine whether predicted exposures from the population PK model could adequately predict the probability of 28-day all-cause mortality, AKI, and clinical response at TOC. Individually predicted exposures to telavancin were derived from the population PK model for telavancin developed in subjects where PK samples were collected.

The HABP/VABP and cSSSI subjects were combined into a single population (defined as Phase 3 subjects) to increase the number of events. Pooling the exposure across the different populations was done with $AUC_{0-24h}$ calculated using a complete PK profile (15 timepoints estimated using the population PK model) in place of the previous value based on 4 sparse samples taken within 12 hours (HABP/VABP) or 4 hours (cSSSI).

Predicted exposure from the population PK model did not have a significant impact on 28-day all-cause mortality in HABP/VABP subjects.

The logistic regression analysis in HABP/VABP subjects with impaired renal function (CrCl≤50 mL/min) is consistent with the results of the CART analysis in HABP/VABP subjects with renal impairment. The CART analysis demonstrated a greater likelihood of 28-day mortality for predicted exposures greater than 767 μg·hr/mL.

3.7 Conclusions

In HABP/VABP subjects with renal impairment (CrCl≤50 mL/min), predicted exposure significantly affected the probability of 28-day all-cause mortality, i.e., with increased exposure, there was an increase in the probability of 28-day all-cause mortality. However, in all Phase 3 subjects and the subpopulation of HABP/VABP subjects with normal renal function, exposure did not have a significant impact on the probability of 28-day all-cause mortality.

For all Phase 3 subjects and the subpopulation of cSSSI subjects, exposure ($AUC_{0-24h}$) demonstrated a significant impact on the probability of AKI, i.e., with increased exposure, there was an increase in the probability of AKI. Conversely, for the subpopulation of HABP/VABP subjects, exposure did not significantly impact the probability of AKI.

For all Phase 3 subjects and the subpopulations of HABP/VABP and cSSSI subjects, exposure did not significantly affect the probability of clinical response at TOC.

Example 4

Simulations of Pharmacokinetic Exposure to Telavancin in Subjects with a New Dosing Regimen Based on Formula (i)

The objective of this analysis was to estimate the exposure to telavancin from the prior daily dosing regimen (10 mg/kg QD) and a new daily dosing regimen based on formula (i) in subjects in various weight and renal function ranges.

Formula (i) was developed using the clearance (CL) parameter developed in the population PK model for telavancin, i.e., CL (hr/L)=$1.15 \cdot (CrCl/99)^{0.454} \cdot (AGE/46)^{0.173} \cdot (WT/77)^{0.352} \cdot GEND \cdot CSSSI1$ (See, Example 1). Substituting this parameter into the standard PK equation:

$$\text{Dose (mg)} = AUC_{target}(\mu g/mL * hr) * \text{Clearance (L/hr)}$$

and keeping the terms relating to weight and creatinine clearance provided formula (i):

$$\text{Dose (mg)} = AUC_{target} * 1.15 * (WT/77)^{0.352} * (CrCl/99)^{0.454} \quad (i)$$

where:
$AUC_{target}$ is the target area under the concentration curve in μg*hr/mL;
WT is the weight of the patient in kilograms; and
CrCl is the creatinine clearance of the patient in mL/minute.

If desired, the dose calculated by formula (i) can be rounded, for example, to the nearest milligram, 5 milligrams or 10 milligrams. To allow for such rounding, formula (I) provides a range of ±5 mg.

A new dosing regimen based on formula (i) was evaluated in simulated patients and compared to the prior dosing regimen. Telavancin exposures for this new dosing regimen were estimated using the virtual population of HABP/VABP and cSSSI subjects (n=1771) from Example 1. Steady-state exposures were estimated based on a total of 100 simulations following the administration of telavancin.

Figure 18:
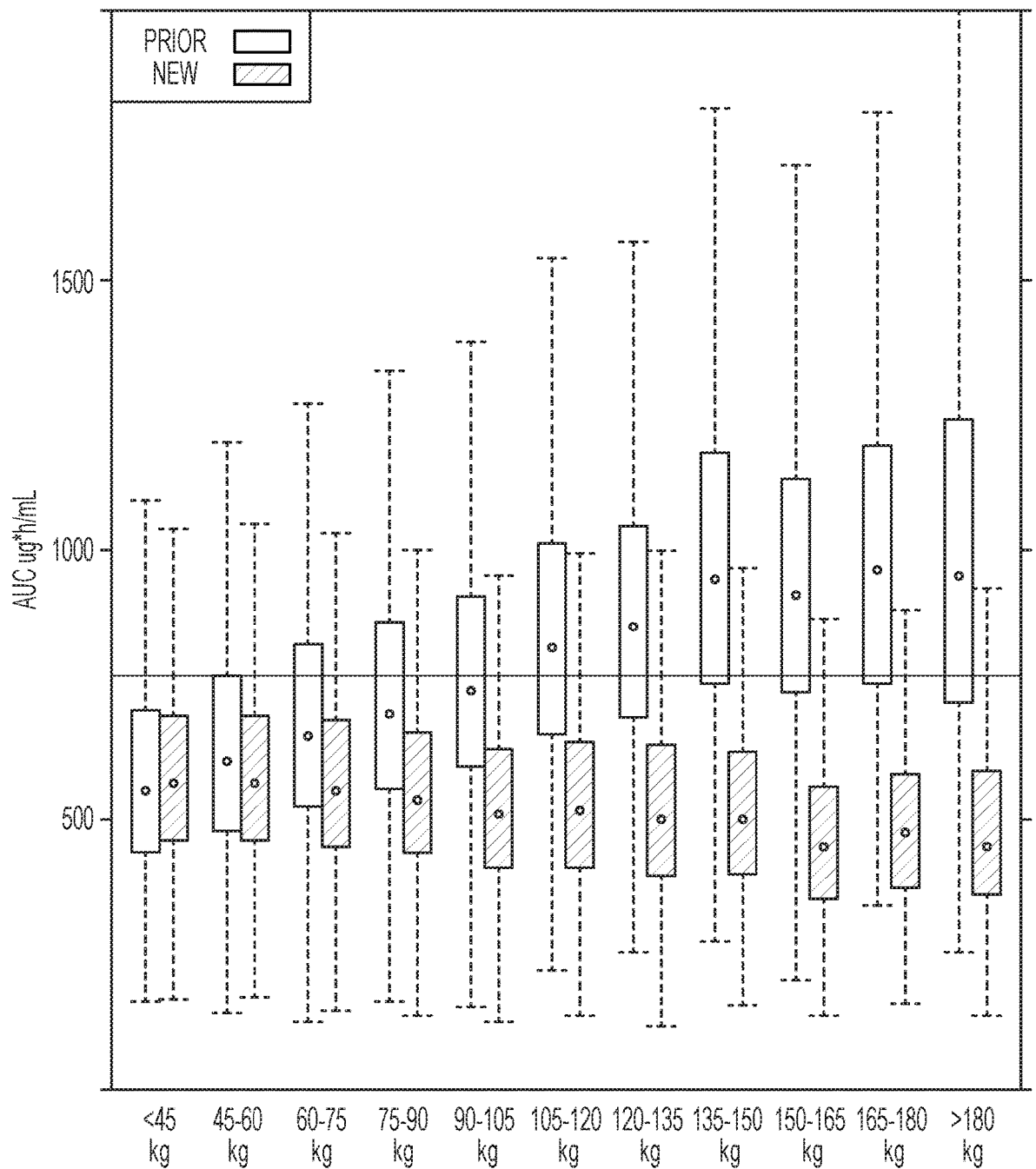
FIG. 18 shows a comparison of predicted exposures (AUC) for various subject weight ranges for the prior dosing regimen and a new dosing regimen of the present invention based on formula (i).
Figure 19:
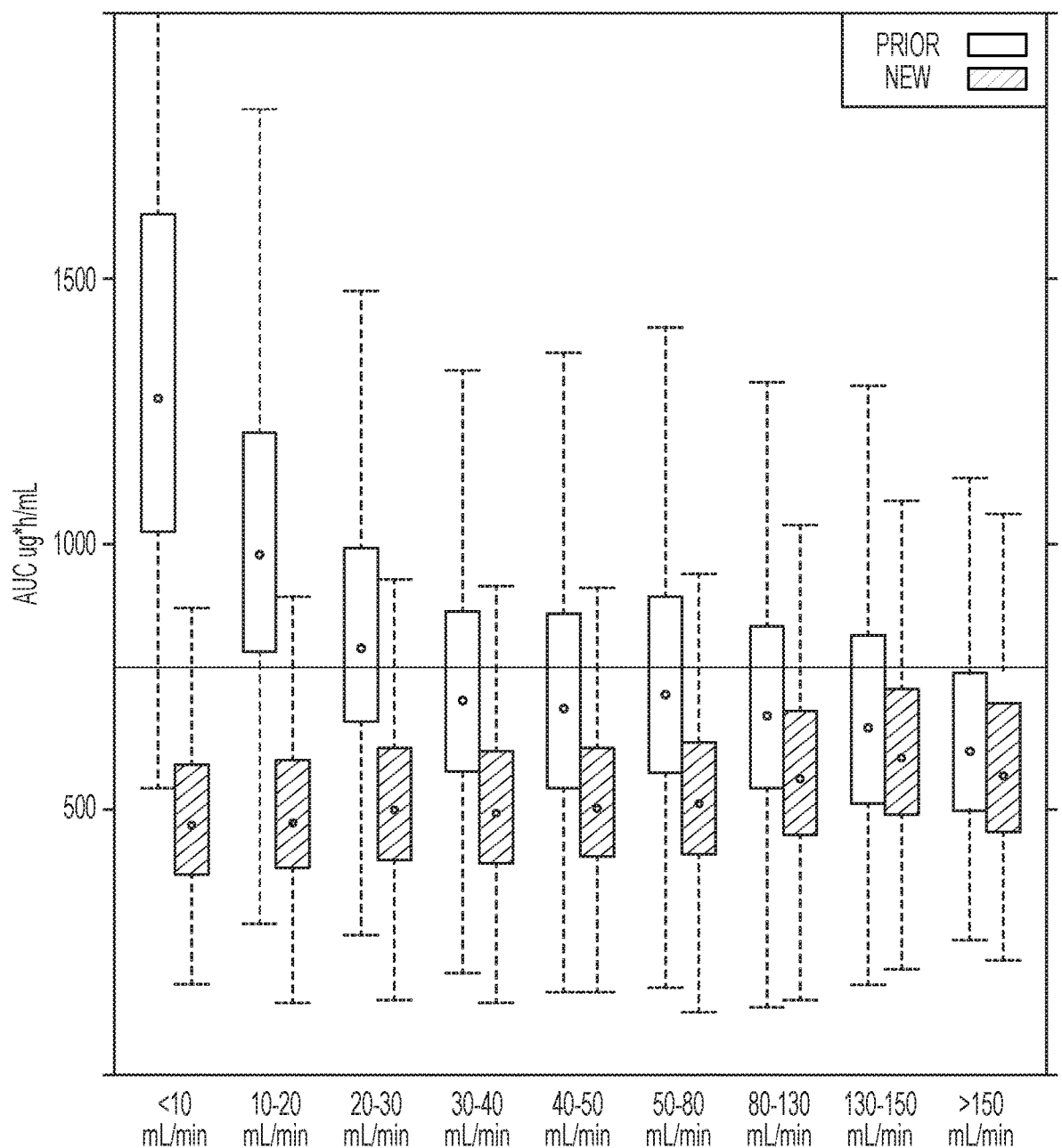
FIG. 19 shows a comparison of predicted exposures (AUC) for various subject renal function ranges for the prior dosing regimen and a new dosing regimen of the present invention based on formula (i).

In overweight subjects, the new dosing regimen based on formula (i) is predicted to reduce exposure compared to the prior dosing regimen (FIG. 18). Additionally, in subjects with low renal function, the new dosing regimen based on formula (i) is predicted to reduce exposure compared to the prior dosing regimen (FIG. 19).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method of treating a patient having a creatinine clearance less than 30 mL/minute and having a complicated skin and skin structure infection caused by *Staphylococcus aureus*, comprising intravenously administering a once-daily dose of 3.8 mg/kg of telavancin (free base equivalent) or a pharmaceutically-acceptable salt thereof, provided that the dose does not exceed 380 mg/day.

2. The method according to claim 1, wherein the patient has a creatinine clearance between 10 mL/minute and less than 30 mL/minute.

3. The method according to claim 1, wherein the *Staphylococcus aureus* is methicillin-resistant *Staphylococcus aureus*.

4. The method according to claim 1, wherein the telavancin is administered as a hydrochloride salt.

5. The method according to claim 1, wherein telavancin or a pharmaceutically-acceptable salt thereof is administered in combination with 2-hydroxypropyl-β-cyclodextrin.

* * * * *